(12) United States Patent
Hengerer et al.

(10) Patent No.: US 12,390,282 B2
(45) Date of Patent: Aug. 19, 2025

(54) POSITIONING SUPPORT SYSTEM FOR POSITIONING A MEDICAL DEVICE

(71) Applicant: Siemens Healthineers AG, Forchheim (DE)

(72) Inventors: Arne Hengerer, Moehrendorf (DE); Florian Maier, Buckenhof (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 264 days.

(21) Appl. No.: 17/872,261

(22) Filed: Jul. 25, 2022

(65) Prior Publication Data
US 2023/0031676 A1    Feb. 2, 2023

(30) Foreign Application Priority Data

Jul. 28, 2021 (DE) ............... 10 2021 208 129.0
Jul. 28, 2021 (DE) ............... 10 2021 208 130.4

(51) Int. Cl.
*A61B 34/20* (2016.01)
*A61B 5/055* (2006.01)
(Continued)

(52) U.S. Cl.
CPC .............. *A61B 34/20* (2016.02); *A61B 5/055* (2013.01); *A61B 10/0233* (2013.01);
(Continued)

(58) Field of Classification Search
CPC ............ A61B 10/0233; A61B 17/3403; A61B 2017/3407; A61B 2017/3411;
(Continued)

(56) References Cited

U.S. PATENT DOCUMENTS

| | | |
|---|---|---|
| 2012/0004681 A1 | 1/2012 | Gross |
| 2012/0041446 A1 | 2/2012 | Bojarski et al. |

(Continued)

FOREIGN PATENT DOCUMENTS

| | | |
|---|---|---|
| CN | 103889349 A | 6/2014 |
| CN | 109526206 A | 3/2019 |

(Continued)

OTHER PUBLICATIONS

Birmingham Prostataklinik https://www.birminghamprostateclinic.co.uk/prostate/assessments/template-biopsy/ Stand: Oct. 28, 2020.
(Continued)

*Primary Examiner* — Michael T Rozanski
(74) *Attorney, Agent, or Firm* — Harness, Dickey & Pierce, P.L.C.

(57) ABSTRACT

One or more example embodiments relate to a positioning support system for positioning a medical device based on at least one medical image, the positioning support system comprising at least one channel for the medical device and configured to be pierced with the medical device, the channel configured to be at an acute first angle to a normal of a surface, the channel including a water-containing medium including at least one polymerizable component, the water-containing medium being configured to cure after being pierced with the medical device when the medical device is coated with a polymerization catalyst, wherein the positioning support system is configured to be placed on the surface, and the positioning support system permits the medical device in the water-containing medium to be depicted in the at least one medical image.

25 Claims, 6 Drawing Sheets

(51) Int. Cl.
*A61B 10/02* (2006.01)
*A61B 17/34* (2006.01)
*A61B 34/10* (2016.01)
*A61B 90/00* (2016.01)

(52) U.S. Cl.
CPC .......... *A61B 17/3403* (2013.01); *A61B 34/10* (2016.02); *A61B 2017/3407* (2013.01); *A61B 2017/3411* (2013.01); *A61B 2034/107* (2016.02); *A61B 2090/067* (2016.02); *A61B 2090/374* (2016.02)

(58) Field of Classification Search
CPC ........ A61B 2034/107; A61B 2090/067; A61B 2090/374; A61B 2090/3937; A61B 2090/3954; A61B 34/10; A61B 34/20; A61B 5/055; A61B 5/061
See application file for complete search history.

(56) References Cited

U.S. PATENT DOCUMENTS

| | | |
|---|---|---|
| 2014/0249371 A1 | 9/2014 | Fischvogt |
| 2015/0160310 A1 | 6/2015 | Requardt et al. |
| 2019/0290362 A1 | 9/2019 | Hostettler et al. |
| 2019/0341519 A1 | 11/2019 | Sporysh et al. |
| 2020/0085381 A1 | 3/2020 | Weine et al. |
| 2020/0121392 A1 | 4/2020 | Daniels |
| 2020/0281575 A1 | 9/2020 | Blackman et al. |

FOREIGN PATENT DOCUMENTS

| | | |
|---|---|---|
| CN | 110168749 | 8/2019 |
| DE | 102010025921 A1 | 1/2012 |
| DE | 102021205812 A1 | 12/2022 |
| EP | 3799063 A1 | 3/2021 |
| KR | 20110067772 A | 6/2011 |
| WO | WO 0101845 A2 | 1/2001 |

OTHER PUBLICATIONS

Urologist Bhobal http://www.urologistbhopal.com/diagnostic-procedures/transperineal-prostate-biopsy/ Stand: Oct. 28, 2020.

POSITIONING SUPPORT SYSTEM FOR POSITIONING A MEDICAL DEVICE

CROSS-REFERENCE TO RELATED APPLICATION(S)

The present application claims priority under 35 U.S.C. § 119 to German Patent Application No. DE 102021208130.4, filed Jul. 28, 2021, and German Patent Application No. 102021208129.0, filed Jul. 28, 2021, the entire contents of each of which are incorporated herein by reference.

FIELD

Some example embodiments of the present invention relate to a positioning support system for positioning a medical device in dependence on at least one medical image. Some example embodiments of the present invention further relate to a method for positioning a medical device with a positioning support system.

BACKGROUND

It is known to perform a minimally invasive procedure in medicine with the aid of image guidance. Herein, the procedure is monitored by imaging, in particular by real-time imaging. During imaging, at least one medical image is acquired. It is known to perform imaging using a magnetic resonance tomography device (acronym: MRT device, also MRI device). In other words, it is known to acquire the medical image during the minimally invasive procedure with an MRT device.

The minimally invasive procedure can, for example, be a biopsy and/or ablation and/or catheterization and/or brachytherapy. During the minimally invasive procedure, a medical device suitable for performing the procedure is inserted into a patient. The medical device is then guided along a path to a target region in which the procedure is to be performed. For this purpose, it is necessary for the medical device to be positioned precisely. Herein, positioning comprises insertion at a position suitable for the procedure, preferably at a predetermined defined angle. In particular, subsequent repositioning of the medical device should be avoided in order to be able to perform the procedure in a time-efficient manner and as gently and painlessly as possible for the patient.

It is known that the medical device is typically not visible in magnetic resonance tomography imaging (acronym: MRT imaging) unless it is marked with an additional contrast agent or an additional contrast agent solution. Thus, the medical device is typically only visible in the medical image acquired with the MRT device when the medical device has been inserted into the patient. In the patient's tissue, the medical device is visible as an artifact in the medical image due to the displacement of the tissue by the medical device. Moreover, if the medical device comprises a magnetizable metal, it generates local magnetic field distortion in the vicinity of the medical device. The magnetic field distortion is generated by a signal drop in the vicinity of the magnetizable metal. This magnetic field distortion is visible as an artifact in the medical image. In particular, the magnetic field distortion generates a dark region around the position of the medical device in the medical image.

For this reason, it is typically not possible to check the positioning, in particular the position and/or angle of the medical device, by MRT imaging prior to the insertion of the medical device into the patient.

It is known to mark the position and/or angle with a finger and to check on the medical image whether the marked position or the marked angle is suitable for the minimally invasive procedure. However, this method is very cumbersome and imprecise because a finger is typically much larger than the medical device. Moreover, a radiologist finds it cumbersome to mark the position and/or angle with a finger while at the same time checking it on the medical image. An additional person for marking the position and/or angle entails additional expenditure on personnel.

In an alternative approach, it is known to mark or project the planned position for inserting the medical device on the patient by at least one laser. This position can then be marked with a marker visible in the medical image and checked in the medical image. With this method, the angle at which the medical device is to be inserted has to be estimated. Here, it is not possible to check the angle prior to insertion of the medical device into the patient.

A further alternative approach is to use a grid that is positioned on the patient relative to the target region. Herein, the grid comprises multiple channels marked with a marker visible in the medical image. To perform the procedure, one of the channels of the grid can be selected and the medical device inserted into the patient through the selected channel. Herein, the channels are typically embodied such that the medical device is inserted perpendicularly into the patient. Thus, the position and angle of the medical device relative to the patient is constrained by the discrete grid. Moreover, it is necessary to position the grid relative to a local coil in an optimal manner in order to ensure that the grid is visible in the medical image. The positioning of the grid and the local coil is sometimes complicated and time-intensive.

SUMMARY

One or more example embodiments of the present invention provide a system that enables flexible positioning of a medical device for performing a minimally invasive procedure with respect to position and angle that can be monitored by MRT imaging.

One or more example embodiments of the present invention provide a positioning support system for positioning a medical device in dependence on at least one medical image and by a method for positioning a medical device with a positioning support unit.

One or more example embodiments relate to a positioning support system for positioning a medical device based on at least one medical image, the positioning support system comprising at least one channel for the medical device and configured to be pierced with the medical device, the channel configured to be at an acute first angle to a normal of a surface, the channel including a water-containing medium including at least one polymerizable component, the water-containing medium being configured to cure after being pierced with the medical device when the medical device is coated with a polymerization catalyst, wherein the positioning support system is configured to be placed on the surface, and the positioning support system permits the medical device in the water-containing medium to be depicted in the at least one medical image.

According to at least one example embodiment, the medical device is a biopsy needle.

According to at least one example embodiment, the water-containing medium comprises at least one of pectin, galantine, agarose, polyacryamide, or polyurethane polymer.

According to at least one example embodiment, the system further includes a holding apparatus for the medical device, wherein the holding apparatus is configured to stabilize the medical device at a second angle relative to the normal to the surface.

According to at least one example embodiment, the system further includes a plate, wherein the channel is a bore in the plate.

According to at least one example embodiment, the channel has a greater width than the medical device, and the channel is configured to be pierced with the medical device at a second angle to the normal to the surface.

According to at least one example embodiment, the system further includes a plurality of channels, wherein the plurality of channels are in a grid-like manner in the plate.

According to at least one example embodiment, the plate includes a coupling apparatus configured to couple the plate to a local coil, wherein the local coil comprises a counterpart to the coupling apparatus.

According to at least one example embodiment, a width of the channel corresponds to an extension of the positioning support system parallel to the surface.

According to at least one example embodiment, the channel is formed by a hollow cylinder.

According to at least one example embodiment, the channel is formed by a body made of the water-containing medium, and the body forms the positioning support system.

According to at least one example embodiment, the body is enclosed by a film, and the film is configured to be pierced with the medical device.

According to at least one example embodiment, the channel is subdivided into a plurality of chambers parallel to the surface by a grid, the water-containing medium is doped with a contrast agent in at least one of the chambers, and the water-containing medium is doped differently in two chambers with at least one common interface.

According to at least one example embodiment, the doped water-containing medium is optically colored in a first color, the non-doped water-containing medium is optically colored in a second color, and the first and the second color are different from one another.

According to at least one example embodiment, the water-containing medium is doped with a contrast agent.

According to at least one example embodiment, at least one of (i) openings of the hollow cylinder are sealed with a film or (ii) the channel is sealed with a film at both openings, and the film is configured to be pierced with the medical device.

According to at least one example embodiment, the system further includes a bonding apparatus, wherein the bonding apparatus is configured to bond the positioning support system on the surface in a releasable manner.

According to at least one example embodiment, a method for positioning the medical device with the positioning support system includes placing the positioning support system on the surface; piercing the channel with the medical device; and acquiring the at least one medical image with a magnetic resonance tomography device, wherein the medical device is visible within the water-containing medium in the medical image.

According to at least one example embodiment, the method further includes checking the positioning of the medical device in the medical image.

According to at least one example embodiment, the method further includes setting a second angle with a holding apparatus for the medical device, wherein the holding apparatus is configured to stabilize the medical device at the second angle relative to the normal to the surface.

According to at least one example embodiment, the water-containing medium cures after the channel has been pierced with the medical device, and the water-containing medium cures to fix the medical device at a second angle.

According to at least one example embodiment, the acquiring acquires a first medical image and the method further comprises determining a position of the at least one channel and a target position in a target region in the first medical image; determining a path of the medical device from the position of the at least one channel to the target position; determining a second angle relative to the normal to the surface, the second angle being an angle at which the medical device is to pierce the at least one channel in order to follow the path; the piercing step including piercing the channel with the medical device at the second angle; acquiring a second medical image with the magnetic resonance tomography device, wherein the medical device is visible in the second medical image within the water-containing medium; and checking in the second medical image whether the positioning of the medical device in the channel is positioned to follow the path.

According to at least one example embodiment, the water-containing medium cures after the piercing, and the curing fixes a second angle of the medical device.

According to at least one example embodiment, the patient support system includes a plurality of channels, the plurality of channels are in a grid-like manner in the plate, the determining the path includes determining at least one path from a position of more than one channel of the plurality of channels to the target position, the determining the second angle determines an angle for each path, wherein the method further comprises classifying the at least one path.

According to at least one example embodiment, the at least one medical image is a magnetic resonance tomography image.

One or more example embodiments of the present invention are described below both with reference to the claimed apparatuses and with reference to the claimed method. Features, advantages or alternative embodiments are likewise also to be transferred to the other claimed subject matter, and vice versa. In other words, the substantive claims (directed, for example, at an apparatus) can also be developed with the features described or claimed in connection with a method. Herein, the corresponding functional features of the method are formed by corresponding substantive modules.

BRIEF DESCRIPTION OF THE DRAWINGS

The above-described properties, features and advantages of one or more example embodiments of the present invention will become clearer and more plainly comprehensible in conjunction with the following figures and the descriptions thereof. Herein, the figures and descriptions are not intended to restrict the invention and the embodiments thereof in any way.

In different figures, identical components are provided with corresponding reference symbols. The figures are generally not true to scale.

In the figures:

FIG. 1 shows a first exemplary embodiment of a positioning support system,

FIG. 2 shows a second exemplary embodiment of a positioning support system,

FIG. 3 shows a third exemplary embodiment of a positioning support system,

Figure 4:
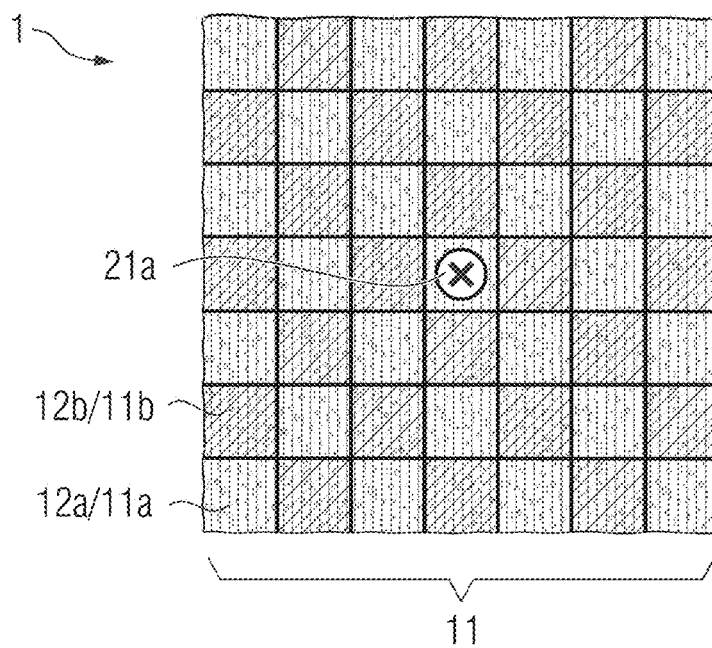
Figure 5:
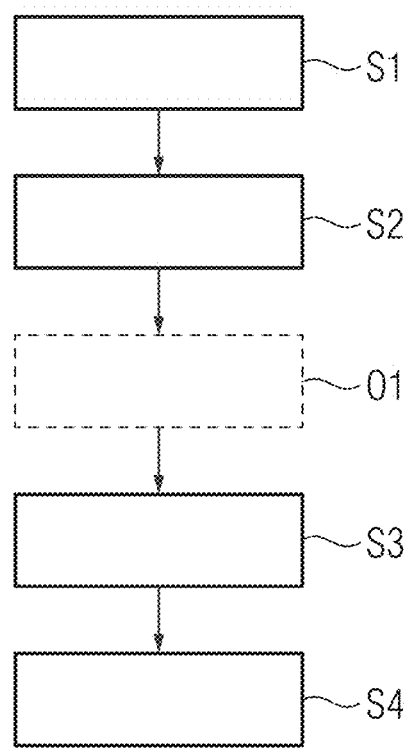
Figure 6:
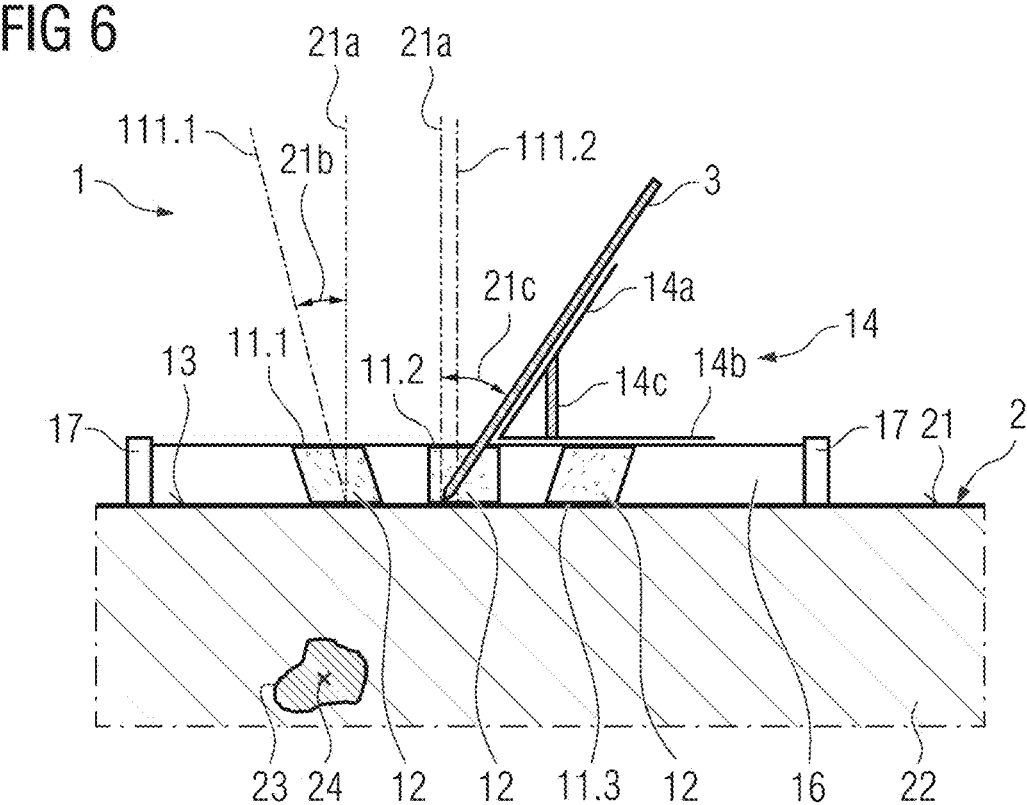
Figure 7:
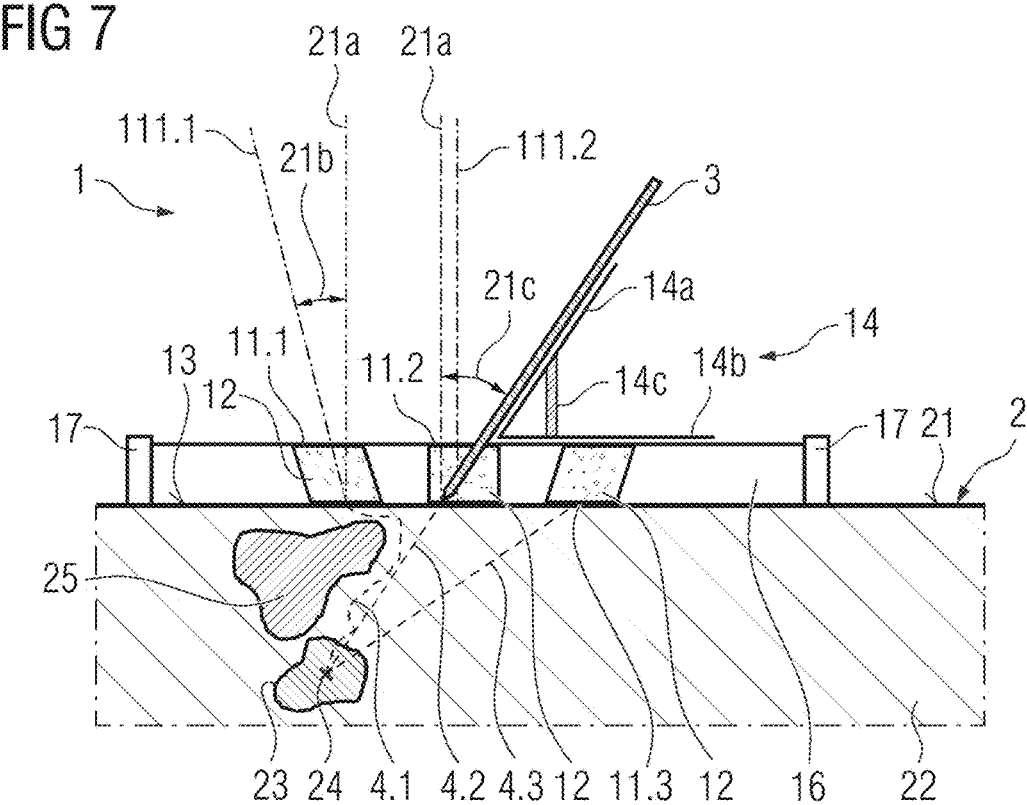
Figure 8:
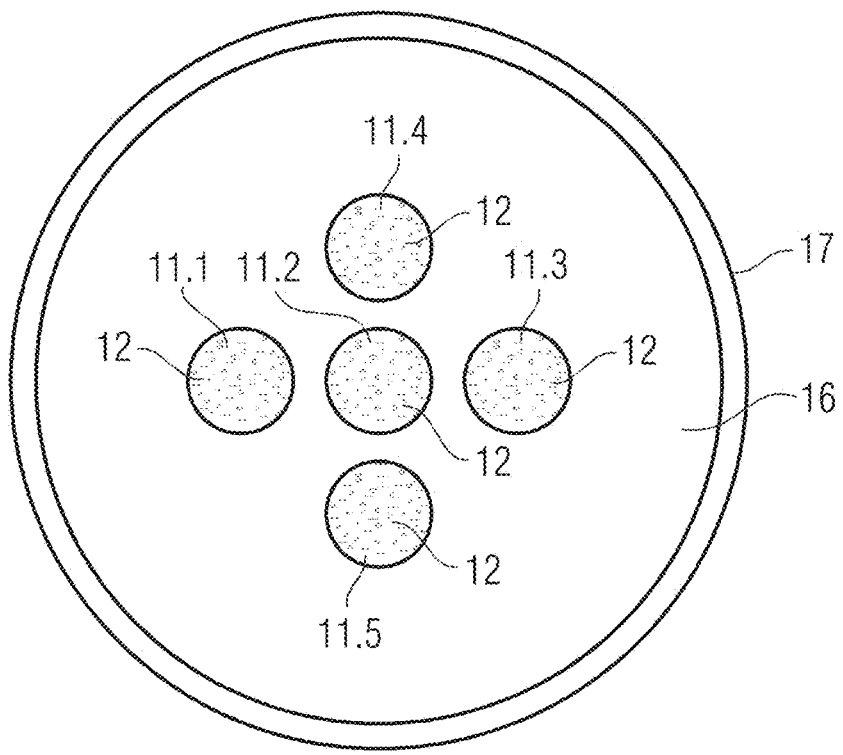
Figure 9:
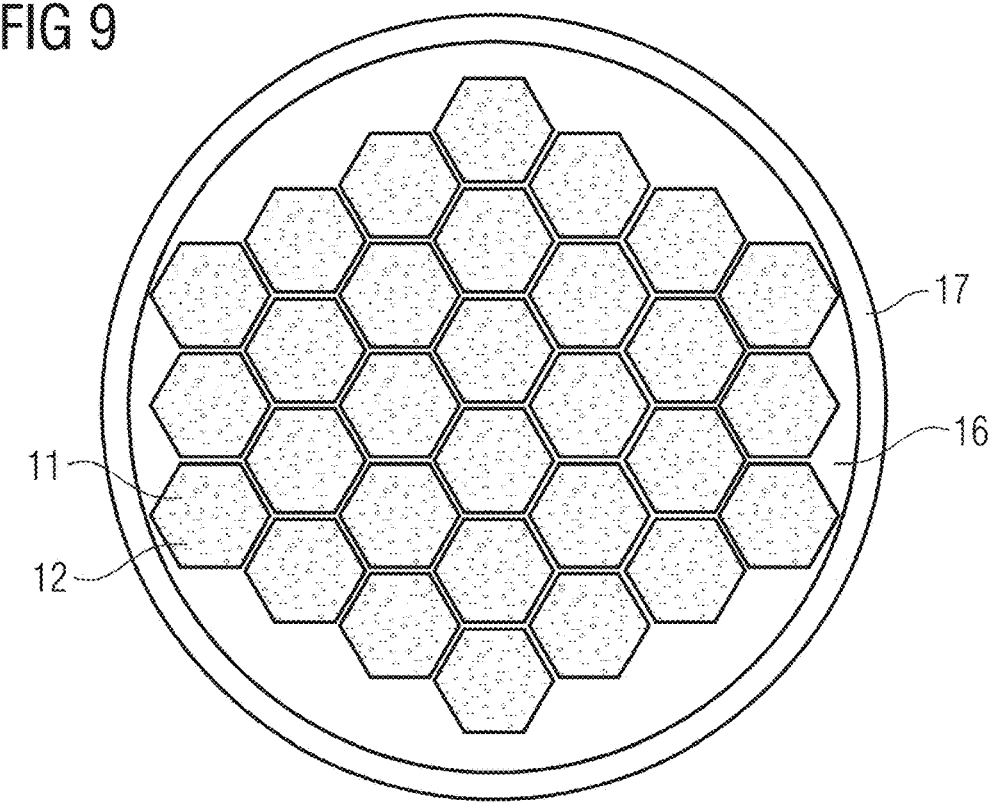
Figure 10:
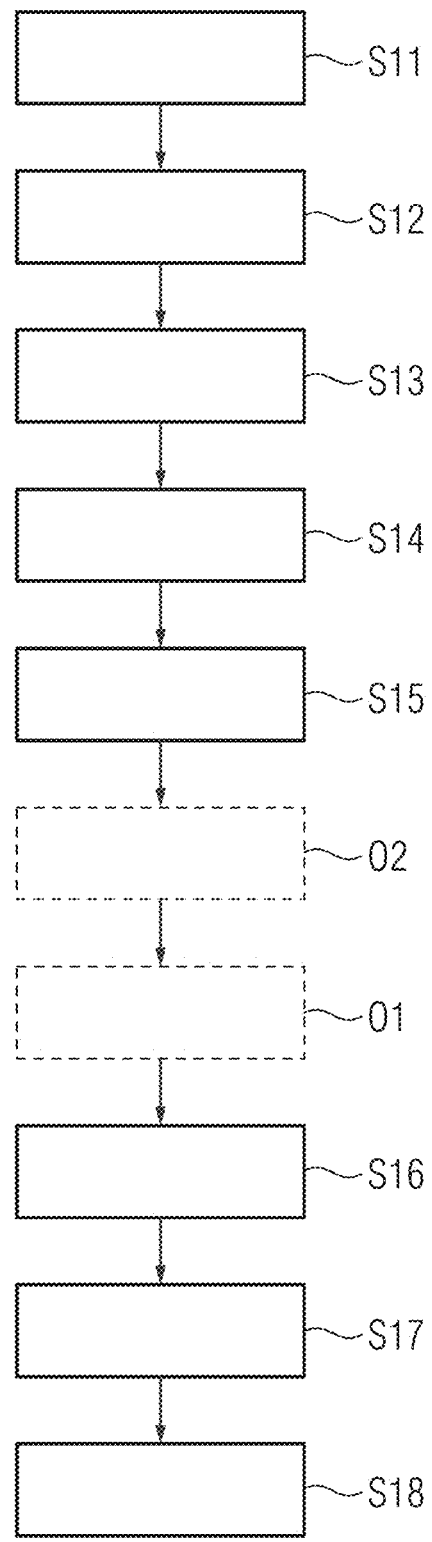

FIG. 4 shows a top view of the third exemplary embodiment of the positioning support system, FIG. 5 shows an exemplary embodiment of a method for positioning a medical device with a positioning support system, FIG. 6 shows a fourth exemplary embodiment of a positioning support system, FIG. 7 shows the fourth exemplary embodiment of the positioning support system with paths, FIG. 8 shows a top view of the fourth exemplary embodiment of the positioning support system, FIG. 9 shows a top view of a fifth exemplary embodiment of the positioning support system, and FIG. 10 shows a second exemplary embodiment of a method for positioning a medical device with a positioning support system.

DETAILED DESCRIPTION

One or more example embodiments of the present invention relates to a positioning support system for positioning a medical device in dependence on at least one medical image. Herein, the medical image is in particular a magnetic resonance tomography image. Herein, the positioning support system is embodied to be placed on a surface. Herein, the positioning support system comprises at least one channel for the medical device. Herein, the channel is embodied at an acute first angle to a normal to the surface or surface normal. Herein, the channel can be pierced with the medical device. Herein, the channel is filled with a water-containing medium. Herein, the medical device in the water-containing medium can be depicted in the medical image.

In particular, the medical device is embodied to be inserted into an object. In other words, the medical device can be embodied to be inserted into a material of which the object consists. Herein, the medical device is inserted into the material through the surface. In other words, the medical device can pierce the surface when inserted into the material. Herein, the surface forms an outer shell of the object. The material in particular can be tissue, in particular human or animal tissue. The object can then be a patient. In other words, the medical device can be inserted into the patient. Herein, the patient can be a human or an animal. The surface then corresponds to a patient's skin.

Herein, the medical device is embodied to perform a minimally invasive procedure. The medical device can in particular comprise a biopsy needle or a catheter or an endoscope or an ablation system or a radiation source for brachytherapy, etc. The medical device in particular can be at least partially made of a metal, for example titanium, medical stainless steel, etc., and/or a plastic. In particular, the medical device can be made of a non-magnetizable or only slightly magnetizable material.

When the medical device is inserted into the object, the medical device must be positioned or aligned in a predetermined manner. Herein, the positioning is defined by a position of the medical device relative to the object and/or by an angle of the medical device relative to the surface. Optionally, the positioning can also comprise an angle that specifies the rotation of the medical device about the normal to the surface as the axis of rotation. In other words, the positioning of the medical device can optionally be specified in spherical coordinates. Herein, the rotation about the normal to the surface as the axis of rotation is described by the azimuth angle. In other words, the azimuth angle describes the angle of rotation of the medical device about the normal to the surface as the axis of rotation. The angle relative to the surface specifies the polar angle of the spherical coordinates. The positioning can be selected optimally for the minimally invasive procedure. In particular, herein, the positioning can depend on a target region of the object in which the procedure is to be performed. In particular, the positioning can also depend on one or more possible critical regions through which the medical device passes on the way from the surface to the target region. A critical region can, for example, be a region with an increased risk of bleeding and/or an organ, etc.

The medical image is acquired with the magnetic resonance tomography (acronym: MRT) device. In other words, the medical image is a magnetic resonance (acronym: MR) image or an MRT image. In particular, the MRT image is a map of a nuclear spin density distribution, preferably of protons in water. The medical image can in particular map at least part of the object. In particular, the medical image can map the region or part of the object into which the medical device is to be inserted. The medical image can map the at least part of the object in two dimensions or three dimensions. In other words, the medical image can be a three-dimensional medical image or a two-dimensional medical slice image. Thus, the medical image can comprise a plurality of pixels or voxels. Herein, the plurality of pixels can be arranged in a two-dimensional pixel matrix. Herein, the plurality of voxels can be arranged in a three-dimensional voxel matrix.

The medical device is not visible or only very faintly visible in the medical image. The medical device is in particular only indirectly visible when it is inserted into and displaces a material visible in the medical image.

The positioning support system is embodied to be placed on the surface. For this purpose, the positioning support system can comprise a contact surface embodied to be in contact with the surface or to be placed thereupon. In particular, the contact surface can be adapted or molded to a shape of the surface. In other words, the contact surface can be embodied as a negative of the surface. The contact surface can, for example, comprise an area between 4 cm2 and 400 cm2. In particular, the contact surface can comprise an area of 4 cm2, 25 cm2, 100 cm2, 225 cm2 or 400 cm2. The positioning support system can in particular comprise a thickness of between 0.5 cm and 5 cm perpendicular to the contact surface. For example, the positioning support system can comprise a thickness of 0.5 cm, 1 cm, 2 cm, 3 cm, 4 cm or 5 cm perpendicular to the contact surface.

Placing on the surface can in particular describe that the positioning support system is placed on the surface. In alternative embodiments, placing the positioning support system can additionally comprise fastening the positioning support system on the object with straps. In alternative embodiments, placing the positioning support system can additionally comprise bonding the positioning support system on the object or the surface thereof. In alternative embodiments, placing of the positioning support system can additionally comprise fastening a positioning support system on the surface with a suction system in particular with a suction cup.

The positioning support system comprises at least one channel. Herein, the channel can comprise a circular or square or oval or elliptical or rectangular cross-sectional area. In other words, the channel can have a circular or square or oval or elliptical or rectangular cross section. Alternatively, the cross-sectional area of the channel can be of any polygonal shape. The channel is in particular elongate or tubular in shape. The channel preferably extends or runs along a rectilinear axis or centerline. The centerline describes a course of the center of the channel. In other words, a course of the channel can be defined by its rectilinear centerline. Herein, the channel extends at the acute first angle to the normal to the surface. Herein, the normal is arranged perpendicular to the surface. In particular, the normal is arranged perpendicular to the contact surface of the positioning support system. The normal to the surface is also referred to in the following as the surface normal. The acute first angle is enclosed by the normal and the channel. Herein, the channel can be represented by the centerline through the center of the channel. In other words, the normal and the centerline enclose the acute first angle. Herein, the acute first angle is between 0° and 90°. In the following, the acute first angle can also be 0°. Alternatively, the acute first angle can, for example, be 1°, 3°, 5°, 10°, 20°, 25° or 50°. An alignment of the channel or the centerline can optionally also be described by a rotation of the channel or centerline about the normal to the surface as the axis of rotation. Herein, the rotation can be specified as an angle parallel to the surface. In this case, the alignment of the channel can be specified in spherical coordinates. Herein, the acute first angle describes the polar angle of the spherical coordinates. The rotation about the normal as the axis of rotation is described by the azimuth angle.

The channel is embodied to enable the medical device to penetrate or pierce the positioning support system at the location of the channel. In other words, the medical device can reach or be guided to the surface through the channel. In other words, before being inserted into the surface or the material bounded by the surface the medical device can be guided through the channel or pierce the channel. Herein, the position of the medical device can be the position at which the medical device pierces the contact surface or at which the medical device pierces the surface of the positioning support system opposite the contact surface. Herein, the surface opposite the contact surface can be aligned parallel to the contact surface. Alternatively, the surface opposite the contact surface can be aligned obliquely to the contact surface.

Herein, the channel is filled with a water-containing medium. Herein, the water-containing medium can in particular have a gelatinous or jelly-like consistency. In other words, the water-containing medium can be embodied such that it remains in the channel and does not run out of the channel. In particular, the consistency of the water-containing medium can be embodied such that the water-containing medium can be pierced with the medical device. In particular, the consistency of the water-containing medium can be embodied such that it stabilizes the positioning of the medical device after being pierced. Then, the positioning can only be changed by the application of a force. The water-containing medium in particular can be a gel. In other words, the water-containing medium can have the consistency of a gel. In particular, the gel can be a disperse system. Herein, the gel can comprise at least two components. The two components can be a solid component and an aqueous component. Herein, the solid component can form a sponge-like three-dimensional network. The pores of this network can be filled by the aqueous component. Such a gel can be referred to as a hydrogel. In other words, the water-containing medium can be a hydrogel. Herein, the water-containing medium can be depicted in the medical image. In other words, the water-containing medium can be depicted with MRT imaging. In other words, the water-containing medium generates a signal in the MRT imaging that can be acquired and depicted in the medical image.

In this case, "piercing" means that the medical device is able to pierce the water-containing medium and can be guided through the channel in this way. In other words, the medical device can at least partially displace and/or compress the water-containing medium such that the medical device can be guided through the channel or is able to pass through or pierce the channel.

The displacement of the water-containing medium by the medical device can be visualized or depicted in the medical image. Moreover, as described above, magnetic field distortion in the vicinity of the medical device caused by a signal drop is visible in the medical image. Signal drop occurs when the medical device comprises a magnetizable metal. In this way, the medical device in the at least one channel can be depicted indirectly in the medical image.

The inventors have recognized that in this way the medical device is visible in the medical image prior to the piercing of the surface or prior to insertion into the material. Thus, the medical device can be inserted into the channel and the positioning, i.e., in particular the position of the medical device and its angle, relative to the surface can be monitored or analyzed in the channel. Thus, the position and/or angle can be corrected without the medical device having to be inserted into the material or object or into the patient. Thus, repositioning is possible, without the patient having to be jabbed several times. This avoids the need to disinfect the medical device multiple times due to multiple insertions into the material. In the case of a medical application, this leads to an improvement of patient comfort and to an acceleration or time saving when performing the minimally invasive procedure.

According to one or more example embodiments of the present invention, the medical device is a biopsy needle.

The biopsy needle can be embodied for tissue sampling. Herein, the material can be tissue, in particular human or animal tissue. The biopsy needle can, for example, be a hollow needle. The biopsy needle can be embodied as rigid or flexible. The biopsy needle can comprise a sharp or blunt tip. In some embodiments of the invention, the biopsy needle can be arranged on a guide wire.

The inventors have recognized that a biopsy needle can be optimally positioned with the aid of the positioning support system even before the insertion or penetration of the biopsy needle through the surface into the patient. The inventors have recognized that in particular patient comfort can be improved or optimized in this way. Moreover, time can be saved, since jabbing the patient multiple times with the biopsy needle due to repositioning may result in the biopsy needle having to be disinfected multiple times. It is also possible to reduce material consumption since it may not be possible to reuse a biopsy needle that has already been inserted into the patient. Monitoring the positioning, in particular the position and/or angle, of the biopsy needle in the channel enables the need to insert the biopsy needle multiple times into the patient to be avoided.

According to one or more example embodiments of the present invention, the water-containing medium comprises at least one of the following materials: pectin, galantine, agarose, polyacryamide, polyurethane polymer.

Said materials can be embodied to form the water-containing medium with the desired consistency.

In particular, the above-described solid component of the water-containing medium can comprise at least one of said materials. In particular, said materials can be embodied to bind a liquid component or to enclose it in their pores, as described above. Herein, the liquid component in particular can be water, in particular distilled water.

The inventors have recognized that said materials are suitable for forming a water-containing medium with the desired consistency. The inventors have recognized that said materials can bind a liquid component. The inventors have also recognized that said materials are also suitable, in particular authorized, for medical use. The inventors have recognized that said materials are visible in the medical image alone or in combination with the liquid component. In other words, the inventors have recognized that said materials can be depicted by MRT imaging alone or in combination with the liquid component. Thus, the medical device is visible in the MRT image when it is introduced into the water-containing medium comprising at least one of the aforementioned materials.

According to one or more example embodiments of the present invention, the medical device is coated with a polymerization catalyst. Herein, the water-containing medium comprises at least one polymerizable component. Herein, the water-containing medium cures after being pierced with the medical device.

The water-containing medium cures due to polymerization of the water-containing medium or the polymerizable component of the water-containing medium. In other words, the water-containing medium polymerizes after being pierced with the medical device. In other words, the polymerizable component of the water-containing medium polymerizes due to contact with the polymerization catalyst. In particular, the piercing of the channel or the water-containing medium initiates polymerization of the water-containing medium. In other words, the contact of the water-containing medium with the polymerization catalyst initiates polymerization of the water-containing medium.

The polymerization catalyst in particular can be a radical starter or a radical-forming initiator. For example, the polymerization catalyst can be polyacrylamide or ammonium persulfate (acronym: APS) or a peroxide or azo compound. Alternatively, the polymerization catalyst can be an ionic initiator.

Herein, the polymerizable component in particular comprises monomers of the polymer to which the polymerizable component or the water-containing medium cures. Herein, the monomers are in particular characterized by at least one double bond. The polymerizable component can in particular comprise dicarboxylic acid and polyhydric alcohols (for example glycerol) or diphenyl carbonate and aromatic diols or vinyl chloride or ethylene.

In this case, "after being pierced" means that the polymerization in particular takes place so slowly that the medical device can be jabbed or guided through the channel before curing is complete. In other words, the medical device can be positioned in the channel before curing.

In the cured state, the water-containing medium can be embodied such that at least the angle of the medical device in the channel is fixed. In other words, the angle can no longer be changed. The angle of the medical device describes the angle assumed by the medical device relative to the surface. In particular, the position of the medical device relative to the positioning support system is also fixed or unchangeable in the fully cured state. Thus, when the positioning support system is not moved relative to the surface, the position of the medical device relative to the surface is also fixed in the fully cured state. In other words, in the fully cured state, the positioning of the medical device can be fixed. Thus, in the cured state, the medical device can in particular only be moved forward and backward. In particular, the medical device can then be inserted into the object through the surface at the fixed angle and fixed position.

The inventors have recognized that curing can prevent the medical device from slipping again after the piercing and the associated positioning of the medical device in the channel. In other words, guidance of the medical device in the channel can be provided by the curing. In this way, it can be ensured that the medical device permanently maintains the desired positioning or the desired position and/or desired angle. In other words, the inventors have recognized that the positioning support system in this way provides a possibility that, after the initial positioning of the medical device in the channel as flexibly as possible, guidance can be provided for the desired positioning. Herein, the guidance for the positioning of the medical device is individual.

According to one or more example embodiments of the present invention, the positioning support system comprises a holding apparatus for the medical device. Herein, the holding apparatus is embodied to stabilize the medical device at a second angle relative to the normal to the surface.

Herein, as described above with regard to the "angle", the second angle defines the alignment or positioning of the medical device relative to the surface. The second angle is enclosed by the normal to the surface and the medical device. The second angle in particular can be an acute angle. The second angle in particular can be 0°.

Herein, the second angle can be equal to the acute first angle. In other words, the magnitude of the second angle can be the same as the magnitude of the acute first angle. In particular, the medical device can then be aligned parallel to the centerline of the channel. Alternatively, the medical device can be rotated relative to the centerline about an angle between 0° and 360° parallel to the surface. In other words, the medical device and the centerline can be rotated about the normal to the surface.

Alternatively, the second angle can be different from the acute first angle. In particular, in this case, the medical device is also aligned obliquely relative to the channel or in the channel when the medical device and the centerline are rotated in the same way relative to the normal to the surface. In particular, herein, the channel has a larger diameter than the medical device.

As described above, the alignment or positioning of the medical device and the centerline can be specified in polar coordinates. Herein, the acute first angle and the second angle in each case correspond to the polar angle or the polar distance angle of the alignment in spherical coordinates. The rotation about the normal to the surface as the axis of rotation can be described by the azimuth angle. When the medical device and the centerline are aligned parallel to one another, the acute first angle is equal to the second angle and the corresponding azimuth angles are also equal.

The holding apparatus is embodied to stabilize the medical device at the second angle. For this purpose, the holding apparatus can form a support between the medical device and the positioning support system. In particular, the holding apparatus then forms a support between the medical device and a surface opposite the contact surface of the positioning support system.

In particular, herein, the holding apparatus can be embodied such that the medical device can be placed on the support. In particular, the support can be embodied as adjustable such that it can support the medical device at an angle corresponding to 90° minus the second angle with respect to the positioning support system. Herein, the holding apparatus in particular can be adjustable by a clamping system or a screw system. The screw system can be used to extend the support of the holding apparatus to a greater or lesser extent. This enables the angle to the positioning support system to be varied. Alternatively, the support can be tensioned with a spring. Adapting the tension of the spring enables the angle supported by the support to be adapted. Herein, the spring can, for example, be a leaf spring or a spiral spring. In some embodiments of the invention, the holding apparatus can be adjustable in an automated manner. In particular, herein, the holding apparatus can comprise a motor embodied to set the acute first angle in an automated manner with the holding apparatus. In particular, for this purpose, the support can be adjusted in an automated manner. In particular, the support can be extended to a greater or lesser extent in an automated manner and hence the acute first angle adapted. In particular, the support can be extended with the motor.

The inventors have recognized that the holding apparatus can be used to stabilize the alignment or positioning of the medical device in the channel. The inventors have recognized that, when the medical device is held manually, the alignment or positioning may possibly be unintentionally less stable. The inventors have also recognized that the holding apparatus allows an operator guiding the medical device to put the medical device down and thus have both hands free. Herein, the operator in particular can be a medical professional or a medical assistant.

According to one or more example embodiments of the present invention, the positioning support system comprises a plate. Herein, the channel is embodied as a bore in the plate.

The plate in particular can be a plastic plate. In other words, the plate can be made of a plastic.

The bore can have two openings in the plate. In other words, the bore can extend transversely through the plate. The bore in particular forms an opening in the contact surface of the positioning support system and an opening in the surface opposite the contact surface of the positioning support system. As described above with respect to the channel, herein, the bore can extend at the acute first angle to the normal to the surface. In particular, the centerline of the bore can form the acute first angle with the normal to the surface. Optionally, as described above, the alignment of the bore can be described by spherical coordinates. In particular, the bore can extend parallel to the normal to the surface.

The inventors have recognized that the channel is easy to implement as a bore in a plate. The inventors have recognized that the plate provides a stable frame for the channel or bore. The inventors have recognized that the plate can be easily and quickly placed on the surface.

According to one or more example embodiments of the present invention, the channel has a greater width than the medical device. Herein, the channel can be pierced with the medical device at a second angle to the normal to the surface.

In particular, the width of the channel is defined by the cross-sectional area or the cross section of the channel. In particular, the width of the medical device is defined by the width of a cross-sectional area or a cross section of the medical device. In particular, the width of the cross-sectional area of the channel or bore can be greater than the width of the cross-sectional area of the medical device. Herein, the width in particular describes a clear width of the corresponding cross-sectional area. The width is defined by the shortest distance between two opposite walls of the cross-sectional area. Herein, the walls form the channel or describe a surface of the medical device. If the channel or the medical device has a circular cross section, the width can be defined by the diameter of the cross section. If the channel or the medical device has a square cross section, the width can be defined by the edge length of the cross section. In particular, the width of the channel can be twice or three times or four times or ten times or twenty times the width of the medical device.

Herein, as described above, the second angle is in particular embodied as described above. Herein, the following applies: the greater the width of the channel or bore relative to the width of the medical device, the greater the second angle can be.

In particular, the second angle can be equal to the acute first angle. In other words, the magnitude of the second angle can be the same as the magnitude of the acute first angle.

Alternatively, the second angle can be different from the acute first angle. In other words, the magnitude of the second angle can be different from the magnitude of the acute first angle. In particular, the medical device can then be aligned obliquely in the channel. In other words, the medical device is then aligned obliquely or at an angle to the centerline of the channel in each rotation about the normal to the surface as the axis of rotation. The greatest possible difference between the second angle and the acute first angle is determined by the ratio of the width of the channel to the width of the medical device and by the thickness of the positioning support system.

The inventors have recognized that the width of the bore or channel can predetermine the flexibility in the positioning of the medical device within the channel. The greater the width of the channel in relation to the width of the medical device, the more flexibly the position and/or the second angle of the medical device in the channel can be selected or set.

According to one or more example embodiments of the present invention, the channel is sealed at both openings with a film. Herein, the film can be pierced with the medical device.

As described above, herein, the openings are in particular formed by the bore. Herein, each of the openings is sealed or closed with the film.

The film in particular can be a plastic film. The film can be at least partially connected to the plate. The film in particular can be fused to the plate, at least partially or in sections. The film in particular can be at least partially connected to the plate at the edge of the opening.

The film in particular can be embodied thin enough to be pierced with the medical device. The film in particular can be embodied such that, when it is pierced with the medical device, it only forms one hole at the puncture site. In other words, the film can be embodied such that it does not tear when pierced with the medical device.

In particular, the film can be embodied such that, when it is pierced with the medical device, it forms a tight enough seal with the medical device to ensure that the water-containing medium cannot flow out at the puncture site. In particular, for this purpose, the film can be embodied as rubber-like and/or flexible.

Herein, the film that seals the opening of the channel in the contact surface of the positioning support system forms at least part of the contact surface of the positioning support system with the surface.

The film is embodied such that it prevents the water-containing medium from running out or flowing out of the channel. Alternatively or additionally, the film prevents soiling and/or contamination of the water-containing medium.

The film in particular can be made of polyester (acronym: PET) or polycarbonate (acronym: PC) or polyvinyl chloride (acronym: PVC) or polyethylene (acronym: PE).

The inventors have recognized that the film can prevent the water-containing medium from being soiled and/or contaminated and/or from flowing out of the channel. The inventors have recognized that sterility of the positioning support system can be ensured in this way.

According to one or more example embodiments of the present invention, the positioning support system comprises a plurality of channels. Herein, the plurality of channels are arranged in a grid-like manner in the plate.

Each channel of the plurality of channels can be embodied like the above-described channel or according to one of the above-described aspects.

Herein, "grid-like" can in particular mean chessboard-like or honeycomb-like.

In particular, herein, in each case two channels are separated from one another by a wall. Herein, the wall is formed by the plate. Herein, the wall can be of any thickness. The wall in particular can be thicker than 0.1 mm. The wall in particular can be thinner than 2 cm. The wall can, for example, be 0.1 mm or 0.5 mm or 1 mm or 1.5 mm or 2 mm or 5 mm or 1 cm or 2 cm thick.

The channels can all form the same acute first angle to the normal to the surface. Alternatively, at least two channels of the plurality of channels can form different acute first angles to the normal to the surface. In particular, the channels at the edge of the plate can form a greater acute first angle with the normal to the surface than the channels arranged more centrally on the plate. In particular, the alignment of the different channels can differ at least partially with respect to their rotation with respect to the normal to the surface as the axis of rotation. In other words, the azimuth angle of the alignment of the different channels can be at least partially different. In particular, for example, all channels can be aligned with a point below the contact surface of the positioning support system. In particular, at least one channel can then form an acute first angle of 0° in the center of the plate.

In some embodiments of the invention, the channels in the center of the plate can be separated from one another by a thinner wall than the channels arranged closer to the edge of the plate.

The inventors have recognized that the plurality of channels enable more flexible positioning of the medical device on the surface. In particular, the position can be selected more flexibly. In particular, in this way, the width of the individual channel can be selected to be sufficiently small to ensure stability of the plate without excessively limiting the selection of the position of the medical device.

According to one or more example embodiments of the present invention, the plate comprises a coupling apparatus for coupling the plate to a local coil, in particular a loop coil or a butterfly coil. Herein, the local coil comprises a counterpart to the coupling apparatus.

In particular, the plate can be coupled to the local coil in a releasable manner. Herein, the coupling apparatus and its counterpart can comprise a plugging and/or a clipping apparatus or clicking apparatus and/or a screwing apparatus. In particular, the coupling apparatus can be plugged and/or clicked and/or screwed together with the counterpart. The plate can be coupled to the local coil such that the plate fills an opening of the local coil. Herein, the local coil is in particular embodied as a loop coil or a butterfly coil.

The inventors have recognized that coupling the plate directly to the local coil enables laborious positioning of the local coil relative to the plate to be avoided. In particular, time can thus be saved when performing or preparing for the minimally invasive procedure. The inventors have recognized that the coupling enables optimal alignment of the local coil with respect to the plate to be ensured and thus the plate or the at least one channel in the plate to be depicted optimally in the medical image. This enables simplified positioning of the medical device based on the medical image with the aid of the positioning support system. The inventors have also recognized that the plate can be disposed of after use, while the local coil can be used multiple times. In some circumstances, this may be necessary to meet medical hygiene standards.

According to one or more example embodiments of the present invention, a width of the channel corresponds to an extension of the positioning support system parallel to the surface.

In other words, the channel, or the cross-sectional area of the channel, comprises the entire area of the positioning support system or the contact surface of the positioning support system. In particular, the positioning support system then only comprises exactly one channel.

The inventors have recognized that the positioning of the medical device is maximally flexible when the width of the channel corresponds to the extension of the positioning support system. The inventors have recognized that then the position of the medical device is only limited by the extension or by the area of the contact surface of the positioning support system. The inventors have recognized that then the second angle of the medical device is only limited by the extension or by the area of the contact surface of the positioning support system and by the thickness of the positioning support system.

According to one or more example embodiments of the present invention, the channel is formed by a hollow cylinder.

In particular, the wall area of the hollow cylinder forms the wall of the channel. In other words, the channel has the shape of a hollow cylinder. The hollow cylinder in particular can be embodied as a "hollow" prism. Herein, the hollow cylinder can comprise any cross-sectional area or any cross section. For example, the hollow cylinder can comprise a circular or a square or an elliptical or an oval or a rectangular cross-sectional area. In particular, the cross-sectional area can form any type of polygon, in particular a pentagon or a tetragon. Alternatively, the cross-sectional area can form a hexagon or octagon. The hollow cylinder has two openings. Herein, the openings have the shape of the cross-sectional area. In other words, the openings comprise the cross-sectional area. One of the openings comprises the contact surface of the positioning support system with the surface.

The hollow cylinder in particular can be made of a plastic. In particular, the hollow cylinder can be made of a transparent plastic. In particular, the transparent plastic can be embodied such that the medical device is visible through the plastic when it is inserted into the channel. In particular, the water-containing medium can then also be embodied as correspondingly transparent.

Alternatively, the hollow cylinder can be made of a metal. In particular, the metal can be a non-magnetizable or slightly magnetizable metal.

The hollow cylinder can be embodied as dimensionally stable. Alternatively, the hollow cylinder can be embodied as easily deformable. In particular, the hollow cylinder can then be embodied such that it is stabilized by the water-containing medium.

The inventors have recognized that a hollow cylinder is suitable for being filled with the water-containing medium. The inventors have also recognized that the hollow cylinder can have any embodiment. In other words, the inventors have recognized that the cross-sectional area of the hollow cylinder can have any embodiment. The inventors have recognized that then, for different minimally invasive procedures, the positioning support system can have a shape with a corresponding cross-sectional area that is particularly suitable for the corresponding minimally invasive procedure. The inventors have recognized that it is helpful for the positioning of the medical device for the medical device to be visible in the channel. The inventors have recognized that the hollow cylinder can be embodied as transparent for this purpose. The inventors have recognized that in this way the minimally invasive procedure can be accelerated and the positioning of the medical device facilitated.

According to one or more example embodiments of the present invention, both openings of the hollow cylinder are sealed with a film. Herein, the film can be pierced with the medical device.

The film in particular can be a plastic film. The film can be connected to the hollow cylinder. The film in particular can be fused with the hollow cylinder, at least partially or in sections.

The film in particular can be embodied thin enough to be pierced with the medical device. The film in particular can be embodied such that, when it is pierced with the medical device, it only forms one hole at the puncture site.

In particular, the film can be embodied such that, when it is pierced with the medical device, it forms a tight enough seal with the medical device to ensure that the water-containing medium cannot flow out at the puncture site. In particular, for this purpose, the film can be embodied as rubber-like and/or flexible.

Herein, one of the two films forms the contact surface of the positioning support system with the surface.

The film is embodied such that it prevents the water-containing medium from running out or flowing out of the hollow cylinder or the channel. Alternatively or additionally, the film prevents soiling and/or contamination of the water-containing medium.

The inventors have recognized that the film can prevent the water-containing medium from being soiled and/or contaminated and/or from flowing out of the hollow cylinder. The inventors have recognized that sterility of the positioning support system can be ensured in this way.

According to one or more example embodiments of the present invention, the channel is formed by a body made of the water-containing medium. Herein, the body forms the positioning support system.

In particular, herein, the water-containing medium is embodied such that it can form a body with a solid shape.

In particular, the body can be solid or non-deformable.

Alternatively, the body can be elastically deformable. In particular, herein, the body can be deformed by the application of pressure. In particular, the shape of the body can adapt to its surroundings. In particular, the body can always return to its original shape when the pressure is removed.

Alternatively, the body can be plastically deformable. Herein, the shape of the body can be individually shaped. In particular, the operator can shape the body such that it is optimally embodied for the corresponding minimally invasive procedure. Herein, the shape of the body can adapt to its surroundings.

In particular, the body can be embodied in the shape of a cushion. In other words, the body can be embodied as a pad.

In particular, the positioning support system can then be embodied as a gel cushion or gel pad.

The inventors have recognized that the shape of the positioning support system embodied in this way can adapt to the surface when it is placed on the surface. The inventors have recognized that in this way it can be ensured that the contact surface of the positioning support system is in contact with the surface as completely as possible or rests flat on the surface. In other words, the positioning support system can adapt to a curved surface. The inventors have recognized that a positioning support system embodied in this way is particularly comfortable for the patient, since it does not cause any pressure points and can adapt to a body shape. The inventors have also recognized that a positioning support system embodied in this way is not subject to any restrictions in terms of shape. In other words, the positioning support system can be embodied in any shape and in this way be optimally embodied for each minimally invasive procedure. The inventors have also recognized that, with a positioning support system embodied in this way, the positioning of the medical device in the channel is not subject to any restrictions. The medical device can be aligned or positioned as desired at any angle on the entire contact surface.

According to one or more example embodiments of the present invention, the body is enclosed by a film. Herein, the film can be pierced with the medical device.

Herein, the film can be embodied as described above. Herein, the film completely encloses the body made of the water-containing medium. In other words, the film forms a surface of the body.

The film in particular can be embodied as transparent. In other words, the film can be embodied such that the medical device is visible through the film when it is inserted into the channel. In particular, the water-containing medium can then also be embodied as transparent.

Herein, the water-containing medium can be embodied as described above with respect to the body. Alternatively, the water-containing medium can be embodied as liquid.

The film in particular can be made of polyester (acronym: PET) or polycarbonate (acronym: PC) or polyvinyl chloride (acronym: PVC) or polyethylene (acronym: PE).

The inventors have recognized that the enclosing film enables the water-containing medium to assume any consistency. The inventors have recognized that the film is easy to sterilize. The inventors have recognized that the film can be used to specify a shape of the body.

According to one or more example embodiments of the present invention, the channel is subdivided into a plurality of chambers parallel to the surface. Herein, the water-containing medium is doped with a contrast agent in at least one of the chambers. Herein, the water-containing medium is doped differently in two chambers with at least one common interface. Herein, the contrast agent in particular comprises gadolinium and/or an iron oxide.

In the following, the term "the chamber is doped" is synonymous with the water-containing medium in the chamber being doped.

Herein, the chambers can be arranged like a chessboard or honeycomb.

Two chambers with a common interface are in particular two chambers arranged next to one another. In other words, two chambers with a common interface are two adjacent chambers.

"Doped differently" can in particular mean that the chambers with at least one common interface are doped with different contrast agents. Alternatively, "doped differently"

can mean that one chamber is doped with the contrast agent and the other chamber adjacent to the at least one common interface is not doped. Alternatively, "doped differently" can mean that a concentration of the contrast agent or the contrast agent concentration in the chambers with at least one common interface is different or not the same. Herein, the contrast agent in the chambers with at least one common interface can be the same contrast agent.

If, for example, the chambers have a chessboard-like arrangement, the water-containing medium is doped with the contrast agent in every second chamber. In different rows or columns, the mutually offset chambers are in each case doped with the contrast agent.

If, in each case, a chamber has more than four interfaces with more than four different chambers, the chambers can be doped with more than one contrast agent such that the water-containing medium in two chambers with a common interface is either doped with different contrast agents or different contrast agent concentrations or that the water-containing medium is not doped with contrast agent in one of the chambers and is doped with contrast agent in the other chamber.

The chambers in particular can be separated from one another by a film embodied as above. In other words, the interface between two chambers can be formed by the film. Herein, the film can extend parallel to the surface normal. Herein, a chamber comprises the entire thickness of the positioning support system and part of the contact surface of the positioning support system. The part of the contact surface in particular can be an area of 1 cm2 or 2.25 cm2 or 4 cm2.

The film in particular can be pierced with the medical device. In other words, the subdivision of the channel can be embodied such that the positioning, in particular the position and/or angle, of the medical device is not restricted thereby.

Herein, the contrast agent is embodied such that it is visible in the medical image. In other words, the contrast agent is an MR contrast agent. In particular, the water-containing medium doped with the contrast agent generates a different signal than the non-doped water-containing medium. Thus, the water-containing medium doped with the contrast agent is depicted differently in the medical image than the non-doped water-containing medium. The contrast agent can in particular comprise gadolinium and/or an iron oxide and/or a manganese compound.

The inventors have recognized that the chambers structure or subdivide the channel in the medical image. The inventors have recognized that in this way, based on the medical image, a suitable chamber can be selected in which the medical device is to pierce the positioning support system. The inventors have recognized that the positioning of the medical device can be simplified in this way. In particular, in this way, the actual position of the medical device in the channel can be determined and implemented and compared in a simplified manner based on the medical image.

According to one or more example embodiments of the present invention, the doped water-containing medium is optically colored in a first color and the non-doped water-containing medium is colored in a second color. Herein, the first and the second color are different from one another.

In the following, the term "the chamber is colored" is synonymous with the term "the water-containing medium in the chamber is colored".

In particular, the first and the second color are easily distinguishable from one another. In particular, the first and the second color are optically distinguishable. In particular, one of the colors can be darker than the other. For example, one of the colors can be blue and the other yellow. Other color combinations are conceivable.

In some embodiments of the invention, only the doped water-containing medium or only the non-doped water-containing medium can be colored with the corresponding color. In other words, either the first color or the second color can be colorless.

If the chambers are doped with more than one contrast agent, for example as described above with respect to chambers with more than four adjacent chambers, the chambers can be colored in more than two different colors.

In particular, the chambers are colored such that two chambers with a common interface are colored with optically different colors.

The inventors have recognized that, in this way, the chambers can be directly optically distinguished. In particular, this enables the different depiction of the chambers in the medical image due to the doping to be transferred to reality, visible to the human eye. The inventors have recognized that the positioning of the medical device can be simplified in this way. In particular, the actual position of the medical device relative to the differently colored chambers of the channel can be compared with the predetermined or optimal position of the medical device relative to the chambers of the channel depicted in the medical image.

According to one or more example embodiments of the present invention, the positioning support system comprises a marking element. The marking element can be fastened on the medical device. Herein, the marking element is visible in the medical image.

The marking element in particular can be a vessel with a contrast agent or a contrast agent solution. Herein, the contrast agent is in particular an MRT contrast agent. In other words, the contrast agent is in particular suitable for MRT imaging. In other words, the contrast agent is visible in the medical image. Herein, the contrast agent is in particular dissolved. The contrast agent is in particular dissolved in water. In other words, the contrast agent can be comprised by a contrast agent solution. The marking element can be fastened on the medical device. Herein, the marking element is in particular fastened such that it does not impede the use of the medical device for the minimally invasive procedure. The marking element in particular can be arranged in a recess of the medical device.

The inventors have recognized that the medical device is visible in the medical image with the aid of the marking element. The inventors have recognized that this further facilitates the positioning of the medical device. In particular, in this way, the medical device can be depicted in the medical image even when the channel is not filled with the water-containing medium.

Preferably, the water-containing medium is doped with a contrast agent. Herein, the contrast agent in particular comprises gadolinium and/or an iron oxide.

Herein, the contrast agent is embodied such that it is visible in the medical image. In other words, the contrast agent is an MR contrast agent or an MRT contrast agent. In particular, the contrast agent is dissolved in the water-containing medium. In particular, the contrast agent or the contrast agent solution generates a signal that can be acquired and depicted in the medical image.

The inventors have recognized that, in this way, the at least one channel or the plurality of channels can be depicted even more clearly in the medical image. The inventors have also recognized that then the displacement of the water-containing medium in the channel or the local distortion of the magnetic field by the medical device when the medical device is inserted into the channel or the channel is pierced with the medical device is also more clearly recognizable in the medical image when the water-containing medium is doped. In other words, the contrast agent enables the medical device in the channel to be indirectly depicted in the medical image in an optimized manner.

According to one or more example embodiments of the present invention, the positioning support system comprises a bonding apparatus. Herein, the bonding apparatus is embodied to fasten the positioning support system on the surface.

In particular, the bonding apparatus is arranged on the contact surface of the positioning support system. The bonding apparatus can comprise at least one bonding point. Alternatively, the bonding apparatus can comprise the entire contact surface. In other words, the entire contact surface can be embodied as a bonding surface or as bonding or as a bonding apparatus.

Herein, the positioning support system is fastened in a releasable manner on the surface with the bonding apparatus.

The inventors have recognized that in this way it is possible to prevent the positioning support system from slipping relative to the surface. The inventors have recognized that bonding is particularly easy and quick to implement. The inventors have also recognized that this does not reduce patient comfort. The inventors have recognized that the bonding enables the positioning support system to be fastened to any location on the patient. In particular, it is thus also possible to place the positioning support system on surfaces that are not aligned geodetically horizontally.

The invention also relates to a method for positioning a medical device with a positioning support system as described above comprising the following method steps:
placing the positioning support system on the surface,
piercing the channel with the medical device,
acquiring a medical image with a magnetic resonance tomography device, wherein the medical device is visible within the water-containing medium in the medical image.

In particular, the method comprises a method step of acquiring a first medical image with a magnetic resonance tomography device. The method in particular comprises a method step of determining a position of the at least one channel and a target position in a target region in the first medical image. The method in particular comprises a method step of determining a path of the medical device from the position of the at least one channel to the target position. The method preferably comprises a method step of determining a second angle relative to the normal to the surface with which the medical device is to pierce the at least one channel in order to follow the path. The method in particular comprises a method step of piercing the channel with the medical device at the second angle. The method especially comprises a method step of acquiring a second medical image with the magnetic resonance tomography device. Herein, the medical device is visible within the water-containing medium in the second medical image. The method in particular comprises a method step of checking in the second medical image whether the positioning of the medical device is embodied such that the medical device can follow the path.

Herein, the positioning support system is embodied as described above. In particular, the positioning support system can be embodied according to one of the described aspects.

In the method step of placing the positioning support system on the surface, the positioning support system is positioned relative to the surface. Herein, the surface is embodied as described above. In particular, the surface forms a surface of an object, in particular a patient. The placing can in particular comprise purely placing and/or fastening. In particular, in the method step of placing, the positioning support system can be fastened or fixed on the object with straps. Alternatively, or additionally, in the method step of placing, the positioning support system can be fastened or fixed on the surface with a bonding apparatus. Alternatively, or additionally, in the method step of placing, the positioning support system can be fastened or fixed on the surface with a suction system, in particular with at least one suction cup. In particular, the positioning support system can be placed together with the local coil. For this purpose, the positioning support system can be coupled to the local coil by the coupling apparatus. The local coil can be placed on the surface in a known manner.

In the method step of acquiring the first medical image, the first medical image is acquired with the MRT device.

In particular, as described above, the first medical image is an MRT image. The at least one channel is visible in the first medical image. Herein, the channel is embodied as described above. In particular, the channel is filled with the water-containing medium as described above. In particular, the water-containing medium in the at least one channel is thus visible or mapped in the medical image. Herein, the water-containing medium is embodied as described above. Herein, the water-containing medium can be doped with a contrast agent as described above.

In the method step of determining the position of the at least one channel and the target position in the target region, the position of the at least one channel and the target position in the first medical image are determined.

Herein, the position of the at least one channel and the target position can be determined with the MRT device. Alternatively, the position of the at least one channel and the target position can be determined with a computer system or a computing unit, in particular an evaluation system. In particular, the position of the at least one channel and the target position can be determined from the medical image by image processing. The position of the at least one channel and the target position can be displayed or provided to an operator by a display unit. Herein, the operator can be a medical professional or a medical assistant. The display unit in particular can be a screen or a monitor.

The position of the at least one channel in particular specifies where the at least one channel is mapped in the first medical image. The position of the at least one channel can be determined by its centerline. In particular, the position of the at least one channel can be defined as the position at which the centerline of the channel intersects the contact surface of the positioning support system. Alternatively, the position of the channel can specify or describe the entire area of the opening of the channel in the contact surface.

If the positioning support system comprises a plurality of channels, the position in the first medical image is determined for each channel.

The target position is the position at which the medical device is to perform the minimally invasive procedure. Herein, the target position is located within the above-described target region. Herein, the medical device and the minimally invasive procedure are embodied as described above.

In the method step of determining the path of the medical device, the path of the medical device is determined from the position of the at least one channel to the target position.

Herein, the path can be determined with the MRT device. Alternatively, the path can be determined with the computer system or the computing unit, in particular the evaluation system. The path can be displayed or provided to the operator by the display unit.

The path specifies how or along which route or path the medical device is to be moved or guided to the target position after entering through the surface. Herein, the path can take into account one or more critical regions through which the medical device should not pass. In other words, the path can be embodied such that it leads from the position of the channel to the target position as directly as possible taking into account possible critical regions. For this purpose, the MRT device or the computer system or the computing unit or the evaluation system can be used to check whether the path intersects a critical region. This check can be based on the medical image. In other words, it can be checked in the medical image whether the path has an intersection with at least one critical region. In particular, the path can be adapted if it intersects a critical region. In particular, the path can then be adapted such that it does not intersect a critical region.

The path can in particular specify the point at which the medical device is to pierce the channel if the channel has a greater width than the medical device. In other words, the path can predetermine the position of the medical device. In particular, the channel can predetermine the position of the medical device when the position of the at least one channel corresponds to the entire area of the opening of the channel in the contact surface. In particular, the position of the medical device then specifies where the medical device is to pierce the channel.

In the method step of determining the second angle relative to the normal to the surface, the second angle at which the medical device is to pierce the at least one first channel, in order to follow the path, is determined.

Herein, the second angle can be determined with the MRT device. Alternatively, the second angle can be determined with the computer system or the computing unit, in particular the evaluation system. The second angle can be displayed or provided to the operator by the display unit.

Herein, the second angle is embodied as described above. Herein, the second angle specifies the angle at which the medical device is to pierce the channel so that it can follow the path.

Optionally, the azimuth angle of the alignment of the medical device can also be determined for the positioning of the medical device. Herein, the azimuth angle is embodied as described above. The azimuth angle is embodied such that the medical device can follow the path. The azimuth angle specifies how the medical device is to be rotated relative to the normal to the surface in order to be able to follow the path.

In the method step of piercing the channel, the medical device pierces or is inserted into the channel at the second angle.

In particular, the medical device can be inserted into the channel taking into account the azimuth angle. In other words, the alignment or positioning of the medical device during the insertion or piercing of the channel can be predetermined or defined by the second angle and optionally by the azimuth angle.

On the piercing of the channel, the medical device is at least partially inserted into the channel. In particular, herein, in this method step, the medical device advantageously does not pierce the surface. Herein, the medical device is inserted into the channel at the position according to the path and at the second angle. Herein, the position and/or the second angle define the positioning of the medical device.

In the method step of acquiring the second medical image, the second medical image is acquired with the MRT device.

In particular, like the first medical image, the second medical image is an MRT image. The medical device is visible within the water-containing medium in the second medical image. In particular, the medical device is at least indirectly visible in the water-containing medium. In other words, the displacement of the water-containing medium in the channel by the medical device is visible or mapped in the second medical image. In particular, due to the magnetic field distortion generated with the medical device which leads to an artifact in the medical image, the medical device is also indirectly visible in the medical image. In particular, the second medical image can map an identical image detail as the first medical image.

In the method step of checking the positioning of the medical device, the positioning of the medical device is checked in the second image.

In particular, it is checked whether the second medical device is positioned such that it can follow the previously determined path. In particular, it can be checked whether the position and the second angle and optionally the azimuth angle of the medical device are embodied such that the medical device can be guided or moved along the path to the target position. In particular, checking includes determining or checking the positioning of the medical device based on the second medical image.

In particular, the checking can take place by image processing. For example, the medical device, the channel and the target position and possibly one or more critical regions in the second medical image can be segmented and the positioning checked on the basis of this segmentation.

In particular, the checking can be performed with the MRT device or with the computer system or the computing unit, in particular the evaluation system. In particular, the display unit can then indicate to the operator whether the positioning of the medical device is correct or whether repositioning is necessary.

In particular, the medical device is not inserted into the object while the positioning of the medical device is being checked. In other words, the medical device has not yet pierced the surface at this time.

The inventors have recognized that path planning based on the first medical image is possible. The inventors have recognized that the at least one channel is visible or mapped on the first medical image. In this way, it is possible to plan the path from the channel to the target position. The inventors have also recognized that the medical device is visible in the second medical image after the insertion or piercing of the channel. The inventors have recognized that it is thus possible to check the positioning of the medical device even before the medical device is inserted into the object. In this way, repositioning of the medical device after the insertion of the medical device into the object can be avoided. This can in particular lead to time and cost savings and increase patient comfort.

According to one or more example embodiments of the present invention, the method also comprises a method step of setting the second angle with the holding apparatus.

Herein, the holding apparatus is embodied as described above.

The second angle in particular can be set before or after piercing or upon piercing of the channel. The second angle in particular can be set in dependence on the path. In other words, the second angle can be set such that the medical device can follow the path. In particular, the second angle can be set automatically with the holding apparatus. In other words, after the determination of the second angle, the holding apparatus can be set such that the medical device is stabilized at the second angle by the holding apparatus.

The inventors have recognized that the second angle can be stabilized with the holding apparatus. In particular, the holding apparatus can prevent an unintentional change to the second angle. It is also possible to set the previously determined precisely second angle with the holding apparatus in a precise manner. In addition, by placing the medical device on the holding apparatus, the operator has both hands free.

According to one or more example embodiments of the present invention, the water-containing medium cures after the channel has been pierced with the medical device. Herein, the curing fixes the medical device at the second angle.

Herein, the curing takes place as described above. In particular, curing takes place in the form of polymerization of the water-containing medium. In particular, herein, the medical device can be at least partially coated with a polymerization catalyst. The polymerization catalyst can initiate polymerization upon contact with the water-containing medium. Herein, the water-containing medium and the polymerization catalyst can be embodied as described above.

The speed of polymerization can define how long the medical device can still be moved or positioned in the channel after the piercing.

The curing fixes the second angle and the position of the medical device. In particular, the positioning of the medical device in the channel is thus fixed. The medical device can then only be moved forward and backward. A forward movement enables the medical device to be inserted into the object through the surface, for example.

The inventors have recognized that the curing fixes the medical device in the channel. In particular, the positioning of the medical device is fixed. In this way an unintentional change to the positioning can be prevented.

According to one or more example embodiments of the present invention, in the method step of determining a path, in each case a path from the position of more than one channel of the plurality of channels to the target position is determined. Herein, in the method step of determining a second angle, the second angle is determined for each path. Herein, the method also comprises a method step of classifying the paths in dependence on their course and/or their mechanical feasibility.

If the positioning support system comprises a plurality of channels, it is in particular possible for the position of more than one channel, in particular each channel, to be determined in the first medical image.

In particular, a path can then be determined from the position of more than one channel to the target position. In particular, a path to the target position from each position, i.e., from each channel, can be determined. Thus, a plurality of paths are determined. Herein, each path can be embodied as described above.

For each path determined, it is possible for the second angle at which the medical device is to be inserted into the corresponding channel or at which it is to pierce the corresponding channel so it can follow the corresponding path to be determined.

In the method step of classifying the paths, the previously determined paths are classified.

During classification, the paths are divided into at least two classes. Herein, the paths are classified in dependence on their course and/or their mechanical feasibility. One of the classes can, for example, be "good" or "suitable" and another "poor" or "unsuitable". Finer gradations are possible for the classification.

In a classification based on the course, a path that extends through a critical region or extends very close to a critical region can, for example, be classified as "poor". A path that bypasses possible critical regions or excludes or reduces damage in a critical region, can be classified as "good".

In a classification based on mechanical feasibility, for example, the spatial course of the path can be taken into account. A path, which, for example, is so greatly curved that the medical device cannot follow this curvature, can, for example, be classified as "poor". Herein, a path that extends almost in a straight line to the target position, is classified as "good". Alternatively or additionally, in the classification based on mechanical feasibility, account can be taken of the feasibility of the previously determined second angle for the path. For example, in some circumstances, a second angle may not be feasible because it is too large and is unfeasible due to the limited width of the corresponding channel and/or the thickness of the positioning support system. In other words, in some circumstances, it may not be possible for the medical device to pierce the channel at the second angle if the second angle is too large. A path for which an unfeasible second angle of this kind has been determined can be classified as "poor". In particular, the width of the corresponding channel and/or the acute first angle which the corresponding channel encloses with the normal to the surface and/or the thickness of the positioning support system can be known for the classification.

The two types of classification can be evaluated in combination and a combined classification created. For example, a path can only be classified as "good" if it is classified as "good" based on both its course and mechanical feasibility.

Herein, the classification can take place with the MRT device. Alternatively, the classification can take place with the computer system or the computing unit, in particular the evaluation system. The result of the classification can be provided or displayed to the operator on the display unit. In particular, the paths can be displayed or depicted or provided to the operator superimposed on the medical image. Herein, for example, paths classified as "good" can be depicted in green and paths classified as "poor" in red. Alternative colors are possible for the depiction of the classification. In particular, the colors can be more finely tuned for finer classification. Alternatively, only paths classified as "good" may be displayed.

The operator can in particular use the classification as the basis for selecting a path by which the minimally invasive procedure is to be performed. In other words, the operator can select which of the paths is to be implemented. In particular, the medical device is then to pierce the channel belonging to the selected path at the position corresponding to the selected path and at the correspondingly determined second angle. The holding apparatus can be set in an automated manner such that the medical device is stabilized at the corresponding second angle during or after the piercing of the channel. Alternatively, the path can be selected in an automated manner based on the classification.

The inventors have recognized that the plurality of channels depict different starting points or initial points for carrying out the minimally invasive procedure. The inventors have recognized that, herein, the channels are differently suitable as starting points in dependence on their position and/or their width and/or their corresponding acute first angle. The inventors have recognized that this can be taken into account by the type of classification of the paths. The operator can then select the most suitable path based on the classification.

According to one embodiment of the invention, the method comprises a method step of placing the positioning support system on the surface, a method step of piercing the channel with the medical device and a method step of acquiring a medical image with a magnetic resonance tomography device, wherein the medical device is visible within the water-containing medium in the medical image. The method in particular also comprises a method step of checking the positioning of the medical device in the medical image. Herein, the positioning support system is embodied as described above. In particular, the positioning support system can be embodied according to one of the described aspects.

In the method step of placing the positioning support system on the surface, the positioning support system is positioned relative to the surface. Herein, the surface is embodied as described above. In particular, the surface forms a surface of an object, in particular a patient. The placing can in particular comprise purely placing and/or fastening. In particular, in the method step of placing, the positioning support system can be fastened or fixed on the object with straps. Alternatively, or additionally, in the method step of placing, the positioning support system can be fastened or fixed on the surface with a bonding apparatus as described above. Alternatively, or additionally, in the method step of placing, the positioning support system can be fastened or fixed on the surface with a suction system, in particular with at least one suction cup.

In the method step of piercing the channel with the medical device, the medical device is in particular inserted into the channel. Herein, the channel is embodied as described above. In particular, the channel is filled with the water-containing medium as described above. The medical device is embodied as described above. Upon piercing of the channel, the medical device is at least partially inserted into the channel. In particular, herein, the medical device advantageously does not pierce the surface. Herein, the medical device is inserted into the channel at a position and at an angle. Herein, the position and/or angle define the positioning of the medical device.

In the method step of acquiring the medical image, the medical image is acquired with the MRT device. In particular, the medical image is an MRT image as described above. In the medical image, the medical device is visible within the water-containing medium. In particular, the medical device is at least indirectly visible in the water-containing medium. In other words, the displacement of the water-containing medium in the channel by the medical device is visible or mapped in the medical image.

In the method step of checking the positioning of the medical device, the positioning of the medical device is verified or checked based on the medical image. In particular, it is checked whether the positioning of the medical device is suitable for performing the minimally invasive procedure. In other words, it is checked whether the medical device can or should be further inserted into the object at the position and at the angle with which it is inserted into the channel in order to perform the minimally invasive procedure. In particular, the checking involves determining or checking the positioning of the medical device based on the second medical image.

In particular, the checking can take place by image processing. For example, the medical device, the channel and the target position and possibly one or more critical regions in the second medical image can be segmented and the positioning checked based on this segmentation.

In particular, the checking can be performed with the MRT device or with a computer system or a computing unit, in particular an evaluation system. In particular, it can then be displayed to the operator by a display unit whether the positioning of the medical device is correct or whether repositioning is necessary. Herein, the display unit can be a screen or a monitor.

The inventors have recognized that the method can be used to check the positioning of the object, in particular the position and/or angle, before the insertion of the medical device. The inventors have recognized that the positioning support system enables the medical device to be visible in the medical image even before insertion into the object. In this way, repositioning of the medical device after the insertion of the medical device into the object can be avoided. This can in particular lead to time and cost savings and increase patient comfort.

According to one or more example embodiments of the present invention, the method also comprises a method step of setting a second angle with the holding apparatus.

Herein, the holding apparatus and the second angle are embodied as described above. In particular, in addition to the position, the second angle defines the positioning of the medical device.

The second angle in particular can be set after the piercing or during the piercing of the channel. The second angle in particular can be set in dependence on the medical image. In other words, the second angle can be adapted in dependence on the positioning of the medical device in the medical image.

The inventors have recognized that the second angle can be stabilized with the holding apparatus. In particular, the holding apparatus can prevent an unintentional change to the second angle. In addition, by placing the medical device on the holding apparatus, the operator has both hands free.

According to one or more example embodiments of the present invention, the water-containing medium cures after the channel has been pierced with the medical device. Herein, the curing fixes the medical device at a second angle.

Herein, the second angle is embodied as described above. Herein, the curing takes place as described above. In particular, the curing takes place in the form of polymerization of the water-containing medium. In particular, herein, the medical device can be at least partially coated with a polymerization catalyst. The polymerization catalyst can initiate polymerization upon contact with the water-containing medium. Herein, the water-containing medium and the polymerization catalyst can be embodied as described above.

The speed of polymerization can define how long the medical device can still be moved or positioned in the channel after the piercing.

The curing fixes the second angle and the position of the medical device. In particular, the positioning of the medical device in the channel is thus fixed. The medical device can then only be moved forward and backward.

The inventors have recognized that the curing fixes the medical device in the channel. In particular, the positioning of the medical device is fixed. In this way, an unintentional change to the positioning can be prevented.

Figure 1:
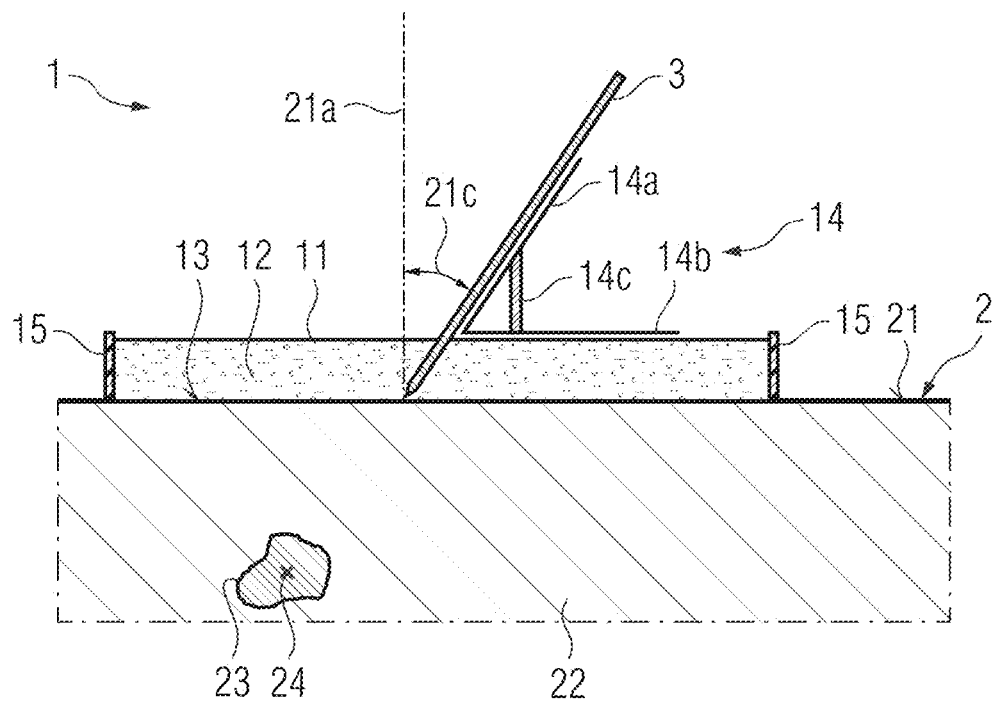

FIG. 1 shows a first exemplary embodiment of a positioning support system 1.

The positioning support system 1 is embodied to be placed on a surface 21. The surface 21 can in particular delimit an object 2. In other words, the surface 21 is the surface of the object 2. The object 2 can be made of a material 22 into which a medical device 3 is to be inserted. The positioning support system 1 is embodied to support positioning of the medical device 3 relative to the object 2. The object 2 in particular can be a patient, in particular a human or an animal. The material 22 can then be human or animal tissue. The surface 21 in particular can then be the skin of the patient.

The medical device 3 is embodied to perform a minimally invasive procedure. The minimally invasive procedure is performed in a target region 23 in the object 2. Herein, in some embodiments of the invention, the medical device 3, can be a biopsy needle. Alternatively, the medical device 3 can, for example, be a catheter, a radiation source for brachytherapy, an endoscope or an ablation system, etc. The minimally invasive procedure can, for example, be tissue sampling, brachytherapy, stent placement, ablation or drainage, etc. For the minimally invasive procedure, the medical device 3 is to be inserted into the surface 21 and guided through the material 22 to a target position 24 in the target region 23. Herein, the medical device 3 is moved along a path to the target position 24. If possible, on the path, the medical device 3 should not pass through and/or damage a critical region. A critical region of the object 2 is, for example, a region with increased risk of bleeding and/or an organ. In order to be able to follow the path, the medical device 3 must be inserted into the object 2 through the surface 21 with suitable positioning. Herein, the positioning is defined by the position of the medical device 3 relative to the object 2 or to the surface 21 and/or by a second angle 21*c*. The second angle 21*c* describes the angle which the medical device 3 forms with the normal 21*a* to the surface 21. Herein, the second angle 21*c* in particular can be an acute angle, i.e., an angle between 0° and 90°. Alternatively, the second angle can be 0°. Optionally, the positioning can additionally be defined by a rotation of the medical device 3 about the normal 21*a* to the surface 21 as the axis of rotation. For this purpose, the positioning can be specified in spherical coordinates. Herein, the second angle 21*c* corresponds to the polar angle of the spherical coordinates. The rotation of the medical device about the normal 21*a* to the surface 21 as the axis of rotation can be described by the azimuth angle of the spherical coordinates.

The medical device 3 cannot be seen or visualized or mapped, or can only be seen or visualized or mapped very weakly, in a medical image acquired by a magnetic resonance tomography (acronym: MRT) device. In other words, the medical device 3 is not directly mapped or only very weakly directly mapped in the medical image. The medical device 3 is indirectly visible or mapped in the medical image when it displaces material that is visible in the medical image. For example, the medical device 3 can be indirectly mapped in the medical image when it is inserted into the material 22 through the surface 21. Herein, the medical image is advantageously an MRT image or an MR image.

When the positioning support system 1 has been placed on the surface 21, the positioning support system 1 rests on the surface 21 with a contact surface 13. The contact surface 13 can be of any size, for example 2 cm2 or 4 cm2 or 9 cm2 or 25 cm2. The positioning support system 1 in particular can be embodied such that it rests stably on the surface 21. In particular, the positioning support system 1 can be adapted or molded to the surface 21. In some embodiments of the invention, the positioning support system 1 can at least approximately map a negative of the surface 21.

During the placing, the positioning support system 1 can be fastened on the surface 21 or on the object 2. For this purpose, in some embodiments of the invention, the positioning support system 1 can comprise a bonding apparatus. Herein, the bonding apparatus is in particular arranged on the contact surface 13. The bonding apparatus is embodied to bond the positioning support system 1 in a releasable manner on the surface 21, at least in points. In particular, the entire contact surface 13 can be embodied as bondable. Alternatively or additionally, during the placing, the positioning support system 1 can be fastened or fixed on the object 2 with at least one strap. Alternatively or additionally, the positioning support system 1 can be fastened on the surface 21 with a suction system. The suction system can comprise at least one suction cup with which the positioning support system 1 can be fastened or fixed in a releasable manner on the surface 21.

The positioning support system 1 comprises a channel 11 that can be pierced with the medical device 3. In alternative embodiments, the positioning support system 1 can also comprise more than one channel 11.

In the exemplary embodiment depicted, the channel 11 is formed by a hollow cylinder 15. Herein, the hollow cylinder 15 in particular forms a wall for the channel 11. The hollow cylinder 15 can in particular comprise a circular or square or elliptical or rectangular cross-sectional area. In particular, the cross-sectional area of the hollow cylinder 15 can embody any shape, in particular any polygon. The hollow cylinder 15 can be made of a plastic. In particular, the hollow cylinder 15 can be made of an optically transparent plastic. Alternatively, the hollow cylinder 15 can be made of a non-magnetizable or only slightly magnetizable metal.

In the exemplary embodiment, the channel 11 is embodied parallel to a normal 21*a* to the surface 21. Alternatively, the channel 11 can enclose an acute first angle with the normal 21*a* to the surface 21.

In the exemplary embodiment depicted, the width of the channel 11 corresponds to an extension of the positioning support system 1 parallel to the surface 21. In other words, the channel 11 comprises almost the entire contact surface 13. In particular, an opening of the channel 11 forms the contact surface 13.

In alternative embodiments, in particular when the positioning support system 1 comprises more than one channel 11, the width of a channel 11 can be less than the extension of the positioning support system 1 parallel to the surface 21.

The channel 11 is filled with a water-containing medium 12. The water-containing medium 12 in particular can be embodied as liquid or jelly-like or gel-like. In particular, the water-containing medium 12 can be embodied such that it does not run out of the channel 11 or out of the hollow cylinder 15. In particular, the water-containing medium 12 can be embodied such that it stabilizes the medical device 3 in the water-containing medium 12 when it is inserted into or pierces the channel 11. In other words, the positioning of the medical device 3 in the water-containing medium 12 embodied in this way can only be changed by the application of a (slight) force or pressure. In this exemplary embodiment, if no force is applied to the medical device 3, it is fixed in the water-containing medium 12 in the corresponding positioning.

In some embodiments of the invention, the water-containing medium 12 can comprise at least one of the following materials: pectin, galantine, agarose, polyacryamide, polyurethane polymer. In particular, the water-containing medium 12 can comprise two components. Herein, one of the two components can embody a solid component and the other component can embody a liquid component. Herein, the solid component in particular can be embodied by one of the aforementioned materials. The solid component can in particular embody a three-dimensional grid structure or a three-dimensional network. The liquid component can be enclosed in pores of this network. Herein, the liquid component can, for example, be water, in particular distilled water.

The water-containing medium 12 is embodied such that it is visible in the medical image. In other words, during magnetic resonance tomography, the water-containing medium 12 generates a signal that can be acquired and mapped in the medical image. When the medical device 3 is inserted into the water-containing medium 12, i.e., into the channel 11, it displaces the water-containing medium 12 at the location. In this way, the medical device 3 can be indirectly visualized in the medical image. In particular, the medical device 3 is thus visible in the medical image before it is inserted into the object 2 through the surface 21.

In this way, positioning of the medical device 3 can be checked in the medical image. In particular, it can be checked whether the positioning of the medical device 3 is suitable for moving the medical device 3 to the target position 24. Herein, it is in particular possible for it to be checked that the medical device 3 does not pass through and/or damage a critical region on the path to the target position 24. Thus, the positioning can be checked and, if necessary, corrected before the medical device 3 is inserted into the object 2.

In some embodiments of the invention, the water-containing medium 12 can cure after being pierced with the medical device 3. In particular, the water-containing medium 12 can polymerize. For this purpose, the medical device 3 can be at least partially coated with a polymerization catalyst. The polymerization catalyst in particular can be a radical starter or a radical-forming initiator. For example, the polymerization catalyst can be polyacrylamide or ammonium persulfate (acronym: APS) or a peroxide or azo compound. Alternatively, the polymerization catalyst can be an ionic initiator. In particular, in this case, the water-containing medium 12 comprises at least one polymerizable component. Herein, the polymerizable component in particular comprises monomers of the polymer to which the polymerizable component or the water-containing medium cures. Herein, the monomers are in particular characterized by at least one double bond. The polymerizable component can in particular comprise dicarboxylic acid and polyhydric alcohols (for example glycerol) or diphenyl carbonate and aromatic diols or vinyl chloride or ethylene. When the water-containing medium 12 comes into contact with the polymerization catalyst, polymerization of the polymerizable component leading to curing of the water-containing medium 12 is activated. The curing fixes the positioning of the medical device 3 after curing. In particular, after curing, the position and the second angle 21c of the medical device 3 can no longer be changed. The medical device 2 can then in particular only be moved forward and backward. A forward movement causes the medical device 3 to be inserted into the object 2.

In an alternative embodiment, depicted here, the medical device 3 can be fixed at the second angle 21c with a holding apparatus 14. For this purpose, the holding apparatus 14 can comprise a support 14c with which the medical device 3 can be supported relative to the surface 21. For this purpose, the support 14c can span an angle of 90° minus the second angle 21c between two legs 14a, 14b of the holding apparatus 14. The angle can be varied by "extending and retracting" the support 14c. To "extend and retract" the support 14c, the length of the support 14c can be varied. For this purpose, the support 14c can be unscrewed to a greater or lesser extent using a screwing apparatus. Alternatively, the support 14c can be embodied as a spring that is tensioned to a greater or lesser extent. The medical device 3 can be placed on one of the legs 14a and thus be stabilized at the second angle 21c.

In some embodiments of the invention, the openings of the hollow cylinder 15 can be sealed with a film. Herein, the film can be pierced with the medical device 3. The film in particular can be embodied to prevent the water-containing medium in the channel from running out and/or being soiled. The film can be at least partially fused with the hollow cylinder at the corresponding opening. The film in particular can be a plastic film.

Figure 2:
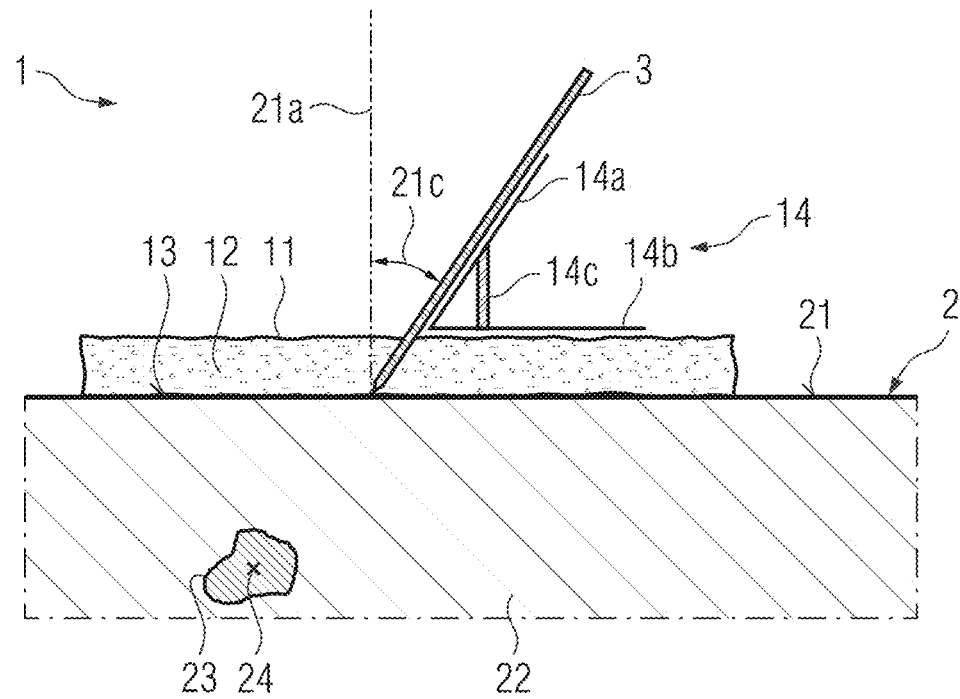

FIG. 2 shows a second exemplary embodiment of a positioning support system 1.

The second exemplary embodiment largely corresponds to the first exemplary embodiment according to FIG. 1 and can also be developed with the embodiments described in this context.

In contrast to the first exemplary embodiment, here, the channel 11 is not formed by a hollow cylinder 15. According to the second exemplary embodiment, the channel 11 is formed by a body made of the water-containing medium 12. Herein, the body forms the positioning support system 1. For this purpose, the water-containing medium 12 can have a solid or jelly-like or gel-like consistency. The water-containing medium 12 can in particular adapt to the shape of the surface 21. In particular, the water-containing medium 12 can be deformable by the action of a force. In other words, the water-containing medium can be embodied as elastic. When the action of the force is removed, the water-containing medium 12 can resume its original shape. Alternatively, the water-containing medium 12 can have a kneadable or plastic consistency. In particular, the water-containing medium 12 can then be formed into any shape.

In some embodiments of the invention, the body formed by the water-containing medium 12 can be enclosed by a film. Herein, the film can be pierced with the medical device 3. The film can in particular determine the shape of the body. The positioning support system 1 can be embodied like a gel cushion or a gel pad.

Figure 3:
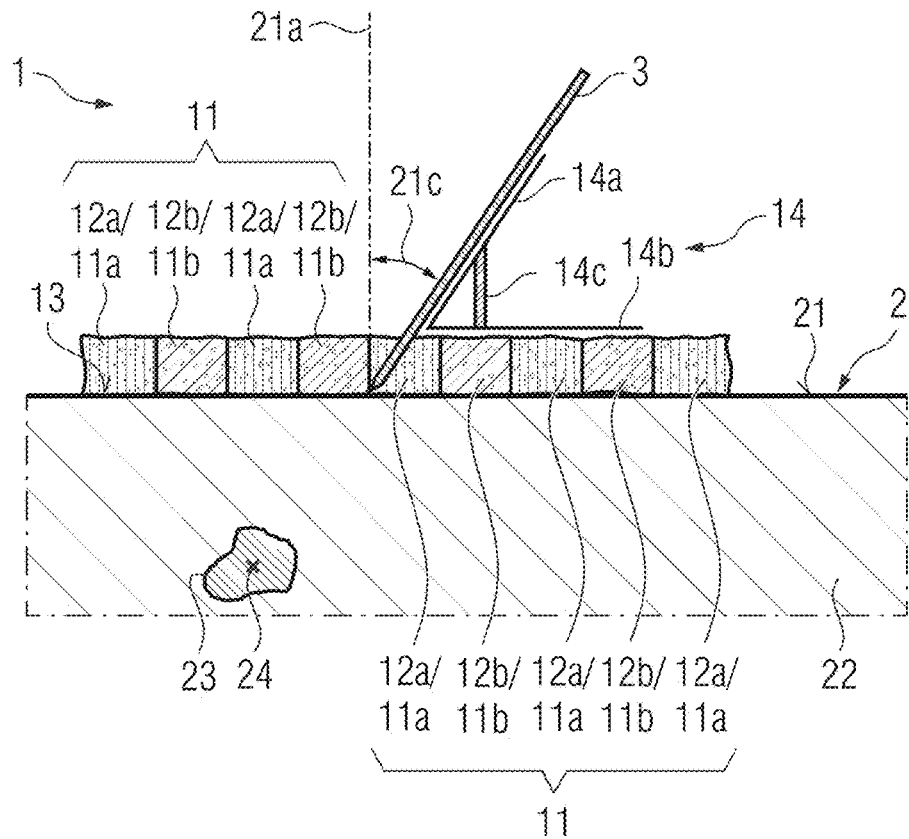

FIG. 3 shows a third exemplary embodiment of a positioning support system 1.

The third exemplary embodiment shows a variant of the second exemplary embodiment according to FIG. 2. Alternatively, in this exemplary embodiment, the channel 11 can be formed by a hollow cylinder 15 as described according to FIG. 1.

The channel 11 is subdivided into a plurality of chambers 11a, 11b parallel to the surface 21 by a grid. In particular, the grid or the subdivision can be implemented with a film. In particular, the film can be embodied to be pierceable with the medical device 3. Herein, the film can be a plastic film. The film in each case forms an interface between two chambers.

In the example depicted, the channel 11 is subdivided into a plurality of chambers 11a, 11b in a chessboard-like style.

Herein, in each case two chambers 11a, 11b with a common interface or two adjacent chambers 11a, 11b are doped differently. In particular, at least one of the chambers 11a, 11b is doped with a contrast agent. Alternatively, a contrast agent concentration in two chambers 11a, 11b with a common interface can be different.

In the exemplary embodiment depicted, the water-containing medium 12a is doped with the contrast agent in every second chamber 11a. The water-containing medium 12b in the other chambers 11b is not doped. Alternatively, the water-containing medium 12 can be doped with a different contrast agent in the other chambers 11b.

In alternative embodiments, the chambers 11a, 11b can, for example, be embodied or arranged in a honeycomb-like style. In particular, more than one contrast agent may then be necessary for doping the chambers 11a, 11b in order to ensure that in each case two adjacent chambers 11a, 11b are doped differently or that one chamber 11a, 11b is not doped and the other chamber 11a, 11b is doped.

The contrast agent is in particular a contrast agent for MRT imaging. The contrast agent generates a signal which is acquired and can be depicted in the medical image. In particular, the water-containing medium 12a doped with the contrast agent thus generates a different signal than the non-doped water-containing medium 12b. In particular, the chambers 11a, 11b are mapped differently in the medical image depending on whether they are filled with doped water-containing medium 12a or non-doped water-containing medium 12b.

In some embodiments of the invention, the doped water-containing medium 12a can be optically colored in a first color. The non-doped water-containing medium 12b can be optically colored in a second color. Herein, the first and the second color are different. In particular, the first and the second color are optically distinguishable. For example, the first color can be blue and the second color yellow or vice versa. Alternatively, the first or second color can be any color. In particular, either the first or the second color can be colorless. In particular, then, correspondingly, either the doped water-containing medium 12a or the non-doped water-containing medium 12b is not colored. In particular, it is in this way possible to optically distinguish the chambers 11a with doped water-containing medium 12a and the chambers 11b with non-doped water-containing medium 12b.

In this way, it is possible to specify the positioning of the medical device 3 in dependence on the chambers 11a, 11b, similarly to as on a chessboard. Herein, the chambers 11a, 11b can be distinguished optically in the medical image by the contrast agent and in some embodiments optically by the first and second color.

If the chambers 11a, 11b are doped differently with more than one contrast agent, the chambers 11a, 11b can be correspondingly colored with more than two optically different colors. In particular, if a chamber 11a, 11b forms more than four interfaces with four different chambers 11a, 11b, the chambers 11a, 11b can be colored in more than two different colors. In particular, the chambers 11a, 11b are then colored such that two chambers 11a, 11b with the same interface are colored differently.

FIG. 4 shows a top view of the third exemplary embodiment of the positioning support system 1.

The chambers 11a, 11b are embodied in a chessboard-like manner. Herein, the water-containing medium 12a, 12b in the chambers 11a, 11b is doped in the individual rows offset to one another.

Alternatively, the chambers 11a, 11b can, for example, be embodied in a honeycomb-like style. In particular, a cross-sectional area of a chamber 11a, 11b can embody any polygonal shape. Herein, in each case, the water-containing medium 12a, 12b in the chambers 11a, 11b is alternately doped in an offset manner or not doped.

FIG. 5 shows an exemplary embodiment of a method for positioning a medical device 3 with a positioning support system 1.

The positioning support system 1 for carrying out the method is embodied according to one of the above-described exemplary embodiments according to FIGS. 1 to 4.

In a method step of placing S1 the positioning support system 1 on the surface 21, the positioning support system 1 is placed on the surface 21. Herein, as described above, the placing S1 can comprise fastening or fixing the positioning support system 1 on the surface 21 or to/on the object 2.

In a method step of piercing S2 the channel 11, the medical device 3 is inserted into the channel 11. In particular, herein, the medical device 3 is introduced into the channel 11 at the second angle 21c to the normal 21a to the surface 21. In particular, the medical device 3 can be introduced into the channel 11 at a suitable position for the minimally invasive procedure. Herein, the insertion into the channel 11 describes the piercing S2 of the channel 11. In particular, in this method step, the medical device 3 can pierce the channel 11 in such a way that it does not damage the surface 21.

In some embodiments of the invention, after the piercing S2 of the channel with the medical device 3, the water-containing medium 12, 12a, 12b with which the channel 11 is filled can cure, as described above. Herein, the medical device 3 is fixed at the second angle 21c by the curing. In particular, the medical device 3 is fixed at the position at which it was introduced into the channel 11. In other words, the positioning of the medical device 3 is fixed by the curing.

In an optional method step of setting O1 the second angle 21c with the holding apparatus 14, the medical device 3 can be stabilized at the second angle 21c with the holding apparatus 14. Herein, the holding apparatus 14 can be embodied as described with respect to FIG. 1. Herein, the angle set by the holding apparatus 14 in particular corresponds to 90° minus the second angle 21c. The optional method step can in particular also be carried out before the piercing S2 of the channel 11.

In a method step of acquiring S3 a medical image, the medical image is acquired with an MRT device. Herein, the medical device 3 within the water-containing medium 12, 12a, 12b is visible or mapped in the medical image. In particular, it is visible in the medical image that the medical device 3 displaces the water-containing medium 12, 12a, 12b in the channel. In other words, the medical device 3 is at least indirectly visible or mapped in the medical image.

In a method step of checking S4 the positioning of the medical device 3, the positioning of the medical device 3 is checked using the medical image. In particular, it can be checked whether the positioning of the medical device 3 is suitable for performing the minimally invasive procedure. In particular, it can be checked whether the medical device 3 is positioned such that it can be guided into the object 2 to the target position 24 along a planned path. Herein, the positioning describes the position and/or the second angle 21c of the medical device 3. Optionally, the positioning can also describe the azimuth angle of the medical device 3.

If necessary, the medical device 3 can be repositioned if it can be identified on the medical image that the positioning of the medical device 3 is not suitable or not optimal. For this purpose, the aforementioned method steps can be repeated as often as desired. In particular, repositioning is thus possible without the medical device 3 having to be repeatedly inserted into the object 2 through the surface 21.

Where this has not explicitly taken place, but is advisable and within the spirit of the invention, individual exemplary embodiments, individual partial aspects or features thereof can be combined with one another or exchanged without departing from the scope of the present invention. Where transferrable, advantages of the invention described with reference to one exemplary embodiment also apply to other exemplary embodiments without explicit mention.

FIG. 6 shows a fourth exemplary embodiment of a positioning support system 1.

The positioning support system 1 is embodied to be placed on a surface 21. The surface 21 can in particular delimit an object 2. In other words, the surface 21 is the surface of the object 2. The object 2 can be made of a material 22 into which a medical device 3 is to be inserted. The positioning support system 1 is embodied to support positioning of the medical device 3 relative to the object 2. The object 2 in particular can be a patient, in particular a human or an animal. The material 22 can then be human or animal tissue. The surface 21 in particular can then be the skin of the patient.

The medical device 3 is embodied to perform a minimally invasive procedure. The minimally invasive procedure is performed in a target region 23 in the object 2. Herein, in some embodiments of the invention, the medical device 3 can be a biopsy needle. Alternatively, the medical device 3 can, for example, be a catheter, a radiation source for brachytherapy, an endoscope or an ablation system, etc. The minimally invasive procedure can, for example, be tissue sampling, brachytherapy, stent placement, ablation or drainage, etc. For the minimally invasive procedure, the medical device 3 is to be inserted into the surface 21 and through the material 22 to a target position 24 in the target region 23. Herein, the medical device 3 is moved along a path 4.2, 4.3, 4.3 to the target position 24. If possible, on the path 4.1, 4.2, 4.3, the medical device 3 should not pass through and/or damage a critical region 25. A critical region 25 of the object 2 is, for example, a region with an increased risk of bleeding and/or an organ. In order to be able to follow the path 4.1, 4.2, 4.3, the medical device 3 must be inserted into the object 2 through the surface 21 with suitable positioning. Herein, the positioning is defined by the position of the medical device 3 relative to the object 2 or to the surface 21 and/or by a second angle 21c. The second angle 21c describes the angle which the medical device 3 forms with the normal 21a to the surface 21. Herein, the second angle 21c in particular can be an acute angle, i.e., an angle between 0° and 90°. Alternatively, the second angle can be 0°. Optionally, the positioning can additionally be defined by a rotation of the medical device 3 about the normal 21a to the surface 21 as the axis of rotation. For this purpose, the positioning can be specified in spherical coordinates. Herein, the second angle 21c corresponds to the polar angle of the spherical coordinates. The rotation of the medical device about the normal 21a to the surface 21 can be described by the azimuth angle of the spherical coordinates.

The medical device 3 cannot be seen or visualized or mapped, or can only be seen or visualized or mapped very weakly, in a medical image which was acquired with a magnetic resonance tomography (acronym: MRT) device. In other words, the medical device 3 is not directly mapped or only very weakly directly mapped in the medical image. The medical device 3 is indirectly visible or mapped in the medical image when it displaces material that is visible in the medical image. For example, the medical device 3 can be indirectly mapped in the medical image when it is inserted into the material 22 through the surface 21. Herein, the medical image is advantageously an MRT image or an MR image.

When the positioning support system 1 has been placed on the surface, the positioning support system 1 rests on the surface 21 with a contact surface 13. The contact surface 13 can be of any size, for example 2 cm2 or 4 cm2 or 9 cm2 or 25 cm2. The positioning support system 1 in particular can be embodied such that it rests stably on the surface 21. In particular, the positioning support system 1 can be adapted or molded to the surface 21. In some embodiments of the invention, the positioning support system 1 can at least approximately map a negative of the surface 21.

During the placing, the positioning support system 1 can optionally be fastened on the surface 21 or on the object 2. For this purpose, in some embodiments of the invention, the positioning support system 1 can comprise a bonding apparatus. Herein, the bonding apparatus is in particular arranged on the contact surface 13. The bonding apparatus is embodied to bond the positioning support system 1 in a releasable manner on the surface 21 at least in points. In particular, the entire contact surface 13 can be embodied as bondable. Alternatively or additionally, during the placing, the positioning support system 1 can be fastened or fixed on the object 2 with at least one strap. Alternatively or additionally, the positioning support system 1 can be fastened on the surface 21 with a suction system. The suction system can comprise at least one suction cup with which the positioning support system 1 can be fastened or fixed in a releasable manner on the surface 21.

The positioning support system 1 comprises at least one channel 11.1, 11.2, 11.3, 11.4, 11.5 that can be pierced with the medical device 3. In the exemplary embodiment depicted, the positioning support system 1 comprises, in cross section, at least three channels 11.1, 11.2, 11.3, 11.4, 11.5. In particular, the positioning support system 1 can comprise a plurality of channels 11.1, 11.2, 11.3, 11.4, 11.5. The plurality of channels 11.1, 11.2, 11.3, 11.4, 11.5 in particular can be arranged in a grid-like manner in a plate 16.

In the following, descriptions and definitions for "the channel" or "the at least one channel" can be transferred to all channels 11.1, 11.2, 11.3, 11.4, 11.5 of the plurality of channels 11.1, 11.2, 11.3, 11.4, 11.5.

Herein, the at least one channel 11.1, 11.2, 11.3, 11.4, 11.5 can be embodied as a bore in the plate 16. Herein, the bore can form two openings in the plate 16. Herein, one of two openings can be arranged in the contact surface 13. The bore can have a cross-sectional area of any shape. For example, the cross-sectional area of the bore can comprise a polygon or a circle or an ellipse.

In some embodiments of the invention, a width of the channel 11.1, 11.2, 11.3, 11.4, 11.5 and hence of the bore can be greater than the width of the medical device 3 that is to pierce the channel 11.1, 11.2, 11.3, 11.4, 11.5. Herein, the width of the channel 11.1, 11.2, 11.3, 11.4, 11.5 is defined by the clear width. The clear width describes the shortest distance between two opposite walls. If the cross-sectional area of the channel 11.1, 11.2, 11.3, 11.4, 11.5 comprises a circle, the width is the diameter of this circle. If the cross-sectional area of the channel 11.1, 11.2, 11.3, 11.4, 11.5 comprises a square, the width is a side length of this square. The width of the medical device 3 is defined by a cross-sectional area of the medical device 3. Here, the width or clear width describes the shortest distance between two opposite points on the surface of the medical device 3. The width of the channel 11.1, 11.2, 11.3, 11.4, 11.5 in particular can be twice or four times or ten times or twenty times the width of the medical device 3.

The channel 11.1, 11.2, 11.3, 11.4, 11.5 can be defined by a centerline 111.1, 111.2. Herein, the centerline 111.1, 111.2 extends through the center of the channel 11.1, 11.2, 11.3, 11.4, 11.5. In particular, the centerline 111.1, 111.2 can specify an alignment of the channel 11.1, 11.2, 11.3, 11.4, 11.5 relative to the surface 21. The channel 11.1, 11.2, 11.3, 11.4, 11.5 in particular extends at an acute first angle 21$b$ to a normal 21$a$ to the surface 21. In other words, the centerline 111.1, 111.2 of the channel 11.1, 11.2, 11.3, 11.4, 11.5 encloses the acute first angle 21$b$ with the normal 21$a$ to the surface 21. Herein, the acute first angle 21$b$ is 0° or between 0° and 90°. The acute first angle 21$b$ of different channels 11.1, 11.2, 11.3, 11.4, 11.5 in particular can be different. For example, all channels 11.1, 11.2, 11.3, 11.4, 11.5 can be aligned such that their midlines 111.1, 111.2 meet at a point in the object 2. In particular, the alignment of a channel 11.1, 11.2, 11.3, 11.4, 11.5 or the centerline 111.1, 111.2 of a channel 11.1, 11.2, 11.3, 11.4, 11.5 can also be described by a rotation or an angle of rotation about the normal 21$a$ to the surface 21 as the axis of rotation. For this purpose, the alignment of the channel 11.1, 11.2, 11.3, 11.4, 11.5 or the centerline 111.1, 111.2 of the channel 11.1, 11.2, 11.3, 11.4, 11.5 can be specified in spherical coordinates. Herein, the acute first angle 21$b$ corresponds to the polar angle of the spherical coordinates and the rotation about the normal 21$a$ to the surface 21 as the axis of rotation is described by the azimuth angle of the spherical coordinates.

The magnitude of the second angle 21$c$ at which the channel 11.1, 11.2, 11.3, 11.4, 11.5 is pierced with the medical device 3 can be the same as or different from the magnitude of the acute first angle 21$b$. In particular, during the piercing of the channel 11.1, 11.2, 11.3, 11.4, 11.5, the medical device 3 can be aligned or positioned parallel to the centerline 111.1, 111.2 thereof or obliquely to the centerline 111.1 thereof, 111.2 or rotated relative to the centerline 111.1, 111.2 thereof. In particular, the alignment of the medical device 3 relative to the centerline 111.1, 111.2 can be rotated about the normal 21$a$ to the surface 21. In particular, the alignment or positioning of the medical device 3 or the alignment of the centerline 111.1, 111.2 can be specified in spherical coordinates as described above. Herein, the acute first angle 21$b$ or the second angle 21$c$ can in each case correspond to the polar angle. The rotation of the alignment about the normal 21$a$ to the surface 21 as the axis of rotation can then be described by a corresponding azimuth angle. When the two polar angles and the two azimuth angles of the alignment of the medical device 3 and the centerline 111.1, 111.2 are the same, the medical device 3 and the centerline 111.1, 111.2 are aligned in parallel. Alternatively, the alignment of the medical device 3 can be rotated relative to the centerline 111.1, 111.2.

In the exemplary embodiment depicted. the plate 16 is coupled to a local coil 17 in a releasable manner via a coupling apparatus. Herein, the local coil 17 in particular can be a loop coil or a butterfly coil. Herein, the plate 16 is in particular arranged in an opening of the local coil 17. Herein, the plate 16 comprises the coupling apparatus. Herein, the local coil 17 comprises a counterpart to the coupling apparatus. The coupling apparatus can in particular comprise a plugging apparatus and/or a clipping apparatus or a clicking apparatus and/or a screwing apparatus. In particular, the coupling apparatus can be plugged and/or clicked or screwed together with the counterpart.

The at least one channel 11.1, 11.2, 11.3, 11.4, 11.5 is filled with a water-containing medium 12. The water-containing medium 12 in particular can be liquid or jelly-like or gel-like. In particular, the water-containing medium 12 can be embodied such that it does not run out of the channel 11.1, 11.2, 11.3, 11.4, 11.5. In particular, the water-containing medium 12 can be embodied such that it stabilizes the medical device 3 in the water-containing medium 12 when it is inserted into or pierces the channel 11.1, 11.2, 11.3, 11.4, 11.5. In other words, the positioning of the medical device 3 in the water-containing medium 12 embodied in this way can only be changed by the application of a (slight) force or pressure. In this exemplary embodiment, if no force is applied to the medical device 3, it is fixed or stabilized in the water-containing medium 12 in the corresponding positioning.

In some embodiments of the invention, the water-containing medium 12 can comprise at least one of the following materials: pectin, galantine, agarose, polyacryamide, polyurethane polymer. In particular, the water-containing medium 12 can comprise two components. Herein, one of the two components can embody a solid component and the other component can embody a liquid component. Herein, the solid component in particular can be embodied by one of the aforementioned materials. The solid component can in particular embody a three-dimensional grid structure or a three-dimensional network. The liquid component can be enclosed in pores of this network. Herein, the liquid component can, for example, be water, in particular distilled water.

The water-containing medium 12 is embodied such that it is visible in the medical image. In other words, during magnetic resonance tomography, the water-containing medium 12 generates a signal that can be acquired and mapped in the medical image. When the medical device 3 is introduced into the water-containing medium 12, i.e., into the channel 11.1, 11.2, 11.3, 11.4, 11.5, it displaces the water-containing medium 12 at the location. In this way, the medical device 3 can be indirectly visualized in the medical image. In particular, the medical device 3 is thus visible in the medical image before it is inserted into the object 2 through the surface 21.

In this way, positioning of the medical device 3 can be checked in the medical image. In particular, it can be checked whether the positioning of the medical device 3 is suitable for moving the medical device 3 to the target position 24. Herein, it in particular can be checked that the medical device 3 does not pass through and/or damage a critical region 25 on the path 4.1, 4.2, 4.3 to the target position 24. Thus, the positioning can be checked and, if necessary, corrected before the medical device 3 is inserted into the object 2.

In some embodiments of the invention, the water-containing medium 12 can cure after being pierced with the medical device 3. In particular, the water-containing medium 12 can polymerize. For this purpose, the medical device 3 can be at least partially coated with a polymerization catalyst. The polymerization catalyst in particular can be a radical starter or a radical-forming initiator. For example, the polymerization catalyst can be polyacrylamide or ammonium persulfate (acronym: APS) or a peroxide or azo compound. Alternatively, the polymerization catalyst can be an ionic initiator. In particular, in this case, the water-containing medium 12 comprises at least one polymerizable component. Herein, the polymerizable component in particular comprises monomers of the polymer to which the polymerizable component or the water-containing medium cures. Herein, the monomers are in particular characterized by at least one double bond. The polymerizable component can in particular comprise dicarboxylic acid and polyhydric alcohols (for example glycerol) or diphenyl carbonate and aromatic diols or vinyl chloride or ethylene. When the water-containing medium 12 comes into contact with the polymerization catalyst, polymerization of the polymerizable component leading to curing of the water-containing medium 12, is activated. The curing fixes the positioning of the medical device 3 after curing. In particular, after curing, the position and the second angle 21*c* of the medical device 3 can no longer be changed. The medical device 2 can then in particular only be moved forward and backward. A forward movement causes the medical device 3 to be inserted into the object 2.

In an alternative embodiment, depicted here, the medical device 3 can be fixed at the second angle 21*c* with a holding apparatus 14. For this purpose, the holding apparatus 14 can comprise a support 14*c* with which the medical device 3 can be fixed relative to the surface 21. For this purpose, the support 14*c* can span an angle of 90° minus the second angle 21*c* between two legs 14*a*, 14*b* of the holding apparatus 14. The angle can be varied by "extending and retracting" the support 14*c*. To "extend and retract" the support 14*c*, the length of the support 14*c* can be varied. For this purpose, the support 14*c* can be unscrewed to a greater or lesser extent using a screwing apparatus. Alternatively, the support 14*c* can be embodied as a spring that is tensioned to a greater or lesser extent. The medical device 3 can be placed on one of the legs 14*a* and thus be stabilized at the second angle 21*c*.

In one embodiment of the invention, the openings of the channel 11.1, 11.2, 11.3, 11.4, 11.5 or the bore forming the channel 11.1, 11.2, 11.3, 11.4, 11.5 can be sealed with a film. Herein, the film is embodied such that it can be pierced with the medical device 3. Herein, the film in particular can be a plastic film. Herein, the film can prevent the water-containing medium 12 from running out of the channel 11.1, 11.2, 11.3, 11.4, 11.5 and/or prevent soiling or contamination of the water-containing medium 12.

In one embodiment of the invention, the water-containing medium 12 can be doped with a contrast agent. Herein, the contrast agent is embodied such that it can be depicted in the medical image. In particular, the water-containing medium 12 doped with the contrast agent can be depicted in the medical image. Thus, the contrast agent is an MRT contrast agent. Herein, the contrast agent in particular comprises gadolinium and/or an iron oxide.

FIG. 7 shows the fourth exemplary embodiment of the positioning support system 1 with paths 4.1, 4.2, 4.3.

The image shows by way of example paths 4.1, 4.2, 4.3 from each of the three channels 11.1, 11.2, 11.3 depicted to the target position 24 in the target region 23. The medical device 3 can be moved along one of the paths 4.1, 4.2, 4.3 to the target position 24. For this purpose, the corresponding channel 11.1, 11.2, 11.3 is to be pierced with the medical device 3 in suitable positioning as described above. The suitable positioning can be checked in the medical image as described above before the medical device 3 pierces the surface 21.

The paths 4.1, 4.2, 4.3 can be embodied to bypass a critical region 25. In other words, the paths 4.1, 4.2, 4.3 are embodied such that, when it is guided along one of the paths 4.1, 4.2, 4.3, the medical device 3 does not pass through or damage the critical region 25. The paths 4.1, 4.2, 4.3 in particular can be determined with the MRT device or with a computer system or a computing unit, in particular an evaluation system. In particular, the paths 4.1, 4.2, 4.3 can be determined based on image processing of the medical image.

The paths 4.1, 4.2, 4.3 can be classified. In particular, the paths 4.1, 4.2, 4.3 can be classified based on their course and/or their mechanical feasibility. In particular, the paths 4.1, 4.2, 4.3 can be classified in at least two classes or categories. For example, the classes can be classified as "good" or "suitable" and "poor" or "unsuitable".

If the paths 4.1, 4.2, 4.3 are classified based on their course, the paths 4.1, 4.2, 4.3 that extend through a critical region 25 or extend very close to a critical region 25 can be classified as "poor" or "unsuitable".

If the paths 4.1, 4.2, 4.3 are classified based on their mechanical feasibility, it is possible to take into account of whether the medical device 3 can follow the path 4.1, 4.2, 4.3 to be classified and/or whether suitable positioning of the medical device 3 is feasible with the positioning support system 1. In the exemplary embodiment depicted, the left path 4.1 is strongly curved in order to bypass the critical region 25. It is possible that the medical device 3 may not be able to follow the path 4.1 due to the strong curvature. In other words, the medical device 3 may be too rigid to follow the path 4.1. For this reason, the path 4.1 can be mechanically unfeasible and classified as "poor" or "unsuitable". In the exemplary embodiment depicted, the right path 4.3 extends at a shallow angle to the surface directly to the target position 24. In other words, the second angle of the right path 4.3 is relatively large. However, due to the width of the channel 11.3 and the thickness of the plate 16 or the positioning support system 1, suitable positioning of the medical device 3 in order to follow the path 4.3 is not possible or feasible. The second angle 21*c* at with which the medical device 3 would have to be inserted into the channel 11.3 as an extension to the path 4.3 is too large. For this reason, this path 4.3 can also be classified as "poor" or "unsuitable".

It appears that the middle path 4.2 is mechanically feasible and does not damage any critical region 25. Thus, this path 4.2 can be assigned to the class "good" or "suitable".

In order to create an overall classification of the paths 4.1, 4.2, 4.3 from the two classifications described, all paths 4.1, 4.2, 4.3 that were classified as "good" or "suitable" can also be classified as "good" or "suitable" in the overall classification. Paths 4.1, 4.2, 4.3 that were classified as "poor" or "unsuitable" in at least one of the above-described classifications can also be classified "poor" or "unsuitable" in the overall classification.

The class of a path 4.1, 4.2, 4.3 or the type of classification can be provided to an operator. Herein, the operator in particular can be the person performing or preparing the minimally invasive procedure. The operator can in particular a medical professional or a medical assistant. The paths 4.1, 4.2, 4.3 can be depicted to the operator superimposed on the medical image by a display unit. Herein, the display unit in particular can be a screen or a monitor. Herein, paths 4.1, 4.2, 4.3 of different classes can be depicted in different colors. For example, paths 4.1, 4.3 of the class "poor" or "unsuitable" can be depicted in red and paths 4.2 of the class "good" or "suitable" in green. Alternative colors or structures of the different classes are conceivable for the depiction of the paths 4.1, 4.2, 4.3. Alternatively, it is also possible for only paths 4.2 classified as "good" or "suitable" to be depicted to the operator.

FIG. 8 shows a top view of the fourth exemplary embodiment of the positioning support system 1.

In the exemplary embodiment depicted, the positioning support system 1 comprises five channels 11.1, 11.2, 11.3, 11.4, 11.5. Alternatively, the positioning support system 1 can also comprise more or fewer than five channels 11.1, 11.2, 11.3, 11.4, 11.5. In other words, the positioning support system 1 comprises a plurality of channels 11.1, 11.2, 11.3, 11.4, 11.5.

Herein, the channels 11.1, 11.2, 11.3, 11.4, 11.5 can be embodied as bores in the plate 16 as described above. The channels 11.1, 11.2, 11.3, 11.4, 11.5 are arranged in a grid-like manner in the plate 16. In the exemplary embodiment depicted, the channels 11.1, 11.2, 11.3, 11.4, 11.5 have a circular cross section or a circular cross-sectional area. In alternative exemplary embodiments, the cross-sectional area of at least one channel 11.1, 11.2, 11.3, 11.4, 11.5 can comprise an alternative shape, for example any polygon or an ellipse.

FIG. 9 shows a top view of a fifth exemplary embodiment of the positioning support system 1.

The positioning support system 1 shows an alternative embodiment to the positioning support system 1 described in FIGS. 6 to 8. The positioning support system 1 depicted here differs from the first exemplary embodiment with respect to the cross-sectional area of the channels 11 and the number of channels 11. The rest of the description of FIGS. 1 to 3 can be transferred analogously to the positioning support system 1 depicted here.

The positioning support system 1 comprises a plurality of channels 11, all of which are filled with the above-described water-containing medium 12. For the sake of clarity, only one channel 11 is provided with the reference symbol in the image. The channels 11 are honeycomb-shaped and arranged in a grid-like manner.

The walls between the channels 11 can be embodied as sufficiently thick to ensure stability of the plate 16. The walls between the channels 11 can be embodied as thin enough to enable the greatest possible flexibility to be provided in the selection of position at which the medical device is to pierce one of the channels 11. The walls can, for example, be 0.1 mm or 0.5 mm or 1 mm or 0.5 cm or 1 cm thick. The thickness of the walls can be variable, in particular when the channels 11 form an acute first angle 21b other than 0° with the normal 21a to the surface 21. In other words, the thickness of a wall between two channels can vary across the thickness of the positioning support system 1 if the acute first angles of the channels and/or their azimuth angle differ. In other words, the thickness of the wall can be embodied variably in the direction of the normal 21a to the surface 21.

FIG. 10 shows a second exemplary embodiment of a method for positioning a medical device 3 with a positioning support system 1.

The positioning support system 1 for carrying out the method is embodied according to one of the above-described exemplary embodiments according to FIGS. 6 to 8.

In a method step of placing S11 the positioning support system 1, the positioning support system 1 is placed on the surface 21. Herein, the placing S10 can comprise fastening or fixing the positioning support system 1 on the surface 21 or to/on the object 2 as described above. In particular, prior to being placed, the plate 16 of the positioning support system 1 can be coupled to a local coil 17 with the coupling apparatus as described above.

In a method step of acquiring S12 a first medical image, the first medical image is acquired with an MRT device. In other words, the first medical image is thus an MRT image. In the first medical image, the positioning support system 1 is in particular mapped on the surface 21. In particular, the target region 23 and the target position 24 can be mapped in the first medical image. In particular, one or more critical regions 25 can also be mapped in the first medical image.

In a method step of determining S13 a position of at least one channel 11, 11.1, 11.2, 11.3, 11.4, 11.5 and the target position 24 in the target region 23, the position of the at least one channel 11, 11.1, 11.2, 11.3, 11.4, 11.5 and the target position 24 are determined in the first medical image. The method step in particular can be carried out with the MRT device and/or with a computer system or a computing unit, in particular an evaluation system. The position of the at least one channel 11, 11.1, 11.2, 11.3, 11.4, 11.5 can be defined by a point of intersection of the centerline 111.1, 111.2 of the at least one channel 11, 11.1, 11.2, 11.3, 11.4, 11.5 with the contact surface 13. Alternatively, the position of the at least one channel 11, 11.1, 11.2, 11.3, 11.4, 11.5 can comprise the entire opening of the channel 11, 11.1, 11.2, 11.3, 11.4, 11.5 in the contact surface. If the positioning support system 1 comprises a plurality of channels 11, 11.1, 11.2, 11.3, 11.4, 11.5, the position of more than one channel 11, 11.1, 11.2, 11.3, 11.4, 11.5, in particular of all channels 11, 11.1, 11.2, 11.3, 11.4, 11.5, can be determined.

In a method step of determining S14 a path 4.1, 4.2, 4.3, a path 4.1, 4.2, 4.3 for the medical device 3 from the position of the channel 11, 11.1, 11.2, 11.3, 11.4, 11.5 to the target position 24 is determined. The method step in particular can be carried out with the MRT device and/or with the computer system or the computing unit, in particular the evaluation system. In particular, a path 4.1, 4.2, 4.3 for the medical device 3 can be determined for more than one channel 11, 11.1, 11.2, 11.3, 11.4, 11.5, in particular for all channels 11, 11.1, 11.2, 11.3, 11.4, 11.5. The path 4.1, 4.2, 4.3 can be embodied such that it forms the shortest possible route from the position of the corresponding channel 11, 11.1, 11.2, 11.3, 11.4, 11.5 to the target position 24 without passing through a critical region 24. During the determination S4 of the path 4.1, 4.2, 4.3, it is in particular possible for the position of the medical device 3 at which the medical device 3 is to pierce the channel 11, 11.1, 11.2, 11.3, 11.4, 11.5 to be determined.

In a method step of determining S15 a second angle 21c, the angle relative to the normal 21a to the surface 21 with which the medical device 3 is to pierce the at least one channel 11, 11.1, 11.2, 11.3, 11.4, 11.5, in order to follow the corresponding path 4.1, 4.2, 4.3, is determined. The method step in particular can be carried out with the MRT device and/or with the computer system or the computing unit, in particular the evaluation system. In particular, the second angle 21c can be determined for more than one channel 11, 11.1, 11.2, 11.3, 11.4, 11.5, in particular for each channel 11, 11.1, 11.2, 11.3, 11.4, 11.5, for which a path 4.1, 4.2, 4.3 has also been determined.

Optionally, it also possible for an azimuth angle for the alignment or positioning of the medical device 3 to be determined. Herein, the azimuth angle specifies a rotation of the medical device 3 about the normal 21a to the surface 21 as the axis of rotation. The azimuth angle is determined such that the medical device 3 can follow the path 4.1, 4.2, 4.3. In particular, the alignment or positioning of the medical device 3 on the piercing of the channel 11, 11.1, 11.2, 11.3, 11.4, 11.5 can then be specified in spherical coordinates.

In an optional method step of classifying O2, the path 4.1, 4.2, 4.3 determined in the method step of determining S14 the path 4.1, 4.2, 4.3 is classified. The method step in particular can be carried out with the MRT device and/or with the computer system or the computing unit, in particular the evaluation system. In particular, all paths 4.1, 4.2, 4.3 are classified in the method step of classifying O2 if more than one path 4.1, 4.2, 4.3 has been determined. The classification of the paths 4.1, 4.2, 4.3 determined in the method step of classifying O2 in particular can be embodied as described with respect to FIG. 2.

In particular, the classification O2 can be based on image processing of the first medical image. Alternatively or additionally, the classification O2 can take place by applying a trained function to the paths 4.1, 4.2, 4.3 and/or the first medical image. The trained function in particular can be based on machine learning or deep learning.

For training the trained function, the trained function can be applied to a plurality of pre-classified paths and first medical images. Herein, the trained function classifies the paths of the plurality of paths. The classification of each path determined by the trained function is compared with the predetermined classification of the corresponding path. The trained function is then adapted such that, in repeated application of the trained function to the paths, the classification determined by the trained function corresponds more closely to the predetermined classification. The training is iteratively repeated until a termination criterion is met. The termination criterion can in particular comprise a minimal similarity between the classification determined by the trained function and the predetermined classification. Alternatively or additionally, the termination criterion can be a maximum number of iterations or adaptations of the trained function.

In an optional method step of setting O1 the second angle 21c, the second angle 21c is set with the holding apparatus 14. If more than one path 4.1, 4.2, 4.3. and thus more than one second angle 21c, has been determined, the second angle 21c of a selected path 4.1, 4.2, 4.3 is set with the holding apparatus 14. In particular, the path 4.1, 4.2, 4.3 can be selected based on the classification. Alternatively or additionally or additionally, the path 4.1, 4.2, 4.3 can be selected based on an operator's personal preference. The selection can in particular take place in an automated manner or made manually by the operator.

Herein, the holding apparatus 14 can be embodied as described with respect to FIG. 6. Herein, the angle set with the holding apparatus 14 in particular corresponds to 90° minus the second angle 21c. In particular, the holding apparatus 14 can be set in an automated manner such that the holding apparatus 14 stabilizes the medical device 3 at the previously determined second angle 21c.

In a method step of piercing S16 the channel 11, 11.1, 11.2, 11.3, 11.4, 11.5, the medical device 3 is inserted into the channel 11, 11.1, 11.2, 11.3, 11.4, 11.5. In particular, herein, the medical device 3 is inserted into the channel 11, 11.1, 11.2, 11.3, 11.4, 11.5 at the second angle 21c to the normal 21a to the surface 21. In particular, the medical device 3 can be inserted into the channel 11, 11.1, 11.2, 11.3, 11.4, 11.5 at a position suitable for the minimally invasive procedure and/or at a suitable second angle 21c and/or a suitable azimuth angle as described above. Herein, the insertion into the channel 11 describes the piercing S2 of the channel 11. In particular, in this method step, the medical device 3 can pierce the channel 11 such that it does not damage the surface 21. In particular, if a plurality of paths 4.1, 4.2, 4.3 have been determined, the medical device 3 is inserted into the channel 11, 11.1, 11.2, 11.3, 11.4, 11.5 corresponding to the selected path 4.1, 4.2, 4.3. The method step of piercing S6 the channel 11, 11.1, 11.2, 11.3, 11.4, 11.5 can in particular also be carried out before the optional setting O1 of the second angle 21c.

In some embodiments of the invention, the water-containing medium 12 with which the channel 11, 11.1, 11.2, 11.3, 11.4, 11.5 is filled can cure after piercing S2 of the channel with the medical device 3 as described above.

Herein, the curing fixes the medical device 3 at the second angle 21c. In particular, the medical device 3 is fixed at the position at which it was introduced into the channel 11. In other words, the positioning of the medical device 3 is fixed by the curing.

In a method step of acquiring S17 a second medical image, the second medical image is acquired with the MRT device. Herein, the medical device 3 in the water-containing medium 12 is mapped or visible in the second medical image. In particular, it is visible in the medical image that the medical device 3 displaces the water-containing medium 12, 12a, 12b in the channel. In particular, the medical device 3 can also be indirectly mapped in the medical image by artifacts. Herein, the artifacts are generated or effected by magnetic field distortion caused with the medical device 3. The medical device 3 generates such magnetic field distortion when it consists at least partially of a metal, in particular a magnetizable metal. In other words, the medical device 3 is at least indirectly visible or mapped in the medical image due to the displacement and/or the magnetic field distortion. In particular, the target position 24 and/or one or more critical regions 25 can also be mapped in the second medical image. In particular, an image detail mapped in the second medical image can correspond to an image detail mapped in the first medical image. In other words, the same details or parts or regions of the object 2 and/or of the positioning support system 1 can be mapped in the first and second medical image.

In a method step of checking S18, it is checked in the second medical image whether the positioning of the medical device 3 is embodied such that it can follow the corresponding path 4.1, 4.2, 4.3. In particular, it can be checked whether the positioning of the medical device 3 is suitable for performing the minimally invasive procedure. In particular, it can be checked whether the medical device 3 is positioned such that it can be guided into the object 2 to the target position 24 along a determined and selected path 4.1, 4.2, 4.3. Herein, the positioning describes the position and/or the second angle 21c of the medical device 3. Optionally the positioning can also describe the azimuth angle of the medical device 3.

The checking S18 can be carried out manually, for example by the operator. Alternatively, the checking S8 in particular can be carried out with the MRT device and/or with a computer system or a computing unit, in particular an evaluation system. In particular, the checking S8 can be based on image processing of the second medical image, in particular segmentation. For the checking S8, in particular the medical device 3, the channel 11, 11.1, 11.2, 11.3, 11.4, 11.5 and/or the target position 24 in the second medical image can be segmented. Additionally, it is also possible for one or more critical regions 25 in the second medical image to be segmented.

The medical device 3 can be repositioned, if necessary, if it can be identified on the medical image that the positioning of the medical device 3 is not suitable or not optimal for following the selected path 4.1, 4.2, 4.3. For this purpose, the aforementioned method steps can be repeated, at least partially, as often as desired. In particular, the method steps of piercing S6 the channel 11, 11.1, 11.2, 11.3, 11.4, 11.5, acquiring S7 the second medical image and checking S8 the positioning of the medical device 3 in the channel 11, 11.1, 11.2, 11.3, 11.4, 11.5 can be carried out iteratively in dependence on the second medical image until the positioning of the medical device 3 is suitable for performing the minimally invasive procedure. In particular, repositioning is thus possible without the medical device 3 having to be repeatedly inserted into the object 2 through the surface 21.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Specific structural and functional details disclosed herein are merely representative for purposes of describing example embodiments of the present invention. This invention may, however, be embodied in many alternate forms and should not be construed as limited to only the embodiments set forth herein.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

Where this has explicitly taken place, but is advisable and within the spirit of the invention, individual exemplary embodiments, individual partial aspects or features thereof can be combined with one another or exchanged without departing from the scope of the present invention. Where transferrable, advantages of the invention described with reference to one exemplary embodiment also apply to other exemplary embodiments without explicit mention.

The invention claimed is:

1. A positioning support system for positioning a medical device based on at least one medical image, the positioning support system comprising:
   at least one channel for the medical device and configured to be pierced with the medical device, the channel configured to be at an acute first angle to a normal of a surface, the channel including,
      a water-containing medium including at least one polymerizable component, the water-containing medium being configured to cure after being pierced with the medical device when the medical device is coated with a polymerization catalyst,
   wherein the positioning support system is configured to be placed on the surface, and
   the positioning support system is configured to permit the medical device in the water-containing medium to be depicted in the at least one medical image.

2. The positioning support system as claimed in claim 1, wherein the medical device is a biopsy needle.

3. The positioning support system as claimed in claim 1, wherein the water-containing medium comprises at least one of pectin, galantine, agarose, polyacryamide, or polyurethane polymer.

4. The positioning support system as claimed in claim 1, further comprising:
   a holding apparatus for the medical device, wherein the holding apparatus is configured to stabilize the medical device at a second angle relative to the normal to the surface.

5. The positioning support system as claimed in claim 1, further comprising:
   a plate, wherein the channel is a bore in the plate.

6. The positioning support system as claimed in claim 5, wherein the channel has a greater width than the medical device, and the channel is configured to be pierced with the medical device at a second angle to the normal to the surface.

7. The positioning support system as claimed in claim 5, further comprising:
   a plurality of channels, wherein the plurality of channels are in a grid-like manner in the plate.

8. The positioning support system as claimed in claim 5, wherein the plate comprises:
   a coupling apparatus configured to couple the plate to a local coil, wherein the local coil comprises a counterpart to the coupling apparatus.

9. The positioning support system as claimed in claim 5, wherein at least one of (i) openings of the channel are sealed with a film or (ii) the channel is sealed with a film at both openings, and the film is configured to be pierced with the medical device.

10. The positioning support system as claimed in claim 1, wherein a width of the channel corresponds to an extension of the positioning support system parallel to the surface.

11. The positioning support system as claimed in claim 10, wherein the channel is formed by a hollow cylinder.

12. The positioning support system as claimed in claim 10, wherein the channel is formed by a body made of the water-containing medium, and the body forms the positioning support system.

13. The positioning support system as claimed in claim 12, wherein the body is enclosed by a film, and the film is configured to be pierced with the medical device.

14. The positioning support system as claimed in claim 10, wherein
   the channel is subdivided into a plurality of chambers parallel to the surface by a grid,
   the water-containing medium is doped with a contrast agent in at least one of the chambers, and
   the water-containing medium is doped differently in two chambers with at least one common interface.

15. The positioning support system as claimed in claim 14, wherein
   the doped water-containing medium is optically colored in a first color,
   a non-doped water-containing medium is optically colored in a second color, and
   the first and the second color are different from one another.

16. The positioning support system as claimed in claim 1, wherein the water-containing medium is doped with a contrast agent.

17. The positioning support system as claimed in claim 1, further comprising:
   a bonding apparatus, wherein the bonding apparatus is configured to bond the positioning support system on the surface in a releasable manner.

18. A method for positioning the medical device with the positioning support system as claimed in claim 1, the method comprising:
   placing the positioning support system on the surface;
   piercing the channel with the medical device; and
   acquiring the at least one medical image with a magnetic resonance tomography device,
   wherein the medical device is visible within the water-containing medium in the medical image.

19. The method as claimed in claim 18, further comprising:
   checking the positioning of the medical device in the medical image.

20. The method as claimed in claim 18, further comprising:
   setting a second angle with a holding apparatus for the medical device, wherein the holding apparatus is configured to stabilize the medical device at the second angle relative to the normal to the surface.

21. The method as claimed in claim 20, wherein the water-containing medium cures after the piercing, and the curing fixes the second angle of the medical device.

22. The method as claimed in claim 18, wherein the water-containing medium cures after the channel has been pierced with the medical device, and the water-containing medium cures to fix the medical device at a second angle.

23. The method as claimed in claim 18, wherein the acquiring acquires a first medical image and the method further comprises:

determining a position of the at least one channel and a target position in a target region in the first medical image;

determining a path of the medical device from the position of the at least one channel to the target position;

determining a second angle relative to the normal to the surface, the second angle being an angle at which the medical device is to pierce the at least one channel in order to follow the path;

the piercing step including, piercing the channel with the medical device at the second angle;

acquiring a second medical image with the magnetic resonance tomography device, wherein the medical device is visible in the second medical image within the water-containing medium; and checking in the second medical image whether the positioning of the medical device in the channel is positioned to follow the path.

24. The method as claimed in claim 23, wherein the positioning support system includes a plurality of channels, the plurality of channels are in a grid-like manner, the determining the path includes, determining at least one path from a position of more than one channel of the plurality of channels to the target position, the determining the second angle determines an angle for each path, wherein the method further comprises:

classifying the at least one path.

25. The system of claim 1, wherein the at least one medical image is a magnetic resonance tomography image.

* * * * *